US008486866B2

(12) United States Patent
Ugolin et al.

(10) Patent No.: US 8,486,866 B2
(45) Date of Patent: Jul. 16, 2013

(54) METHOD FOR THE QUANTITATIVE MEASUREMENT OF BIOMOLECULAR TARGETS DEPOSITED ON A BIOCHIP, AND DEVICE FOR IMPLEMENTING IT

(75) Inventors: Nicolas Ugolin, Paris (FR); Denis Menut, Creteil (FR); Julien Le Meur, Pont-Aven (FR); Pascal Wodling, Orsay (FR); Sylvie Chevillard, Le Kremlin-Bicetre (FR)

(73) Assignee: Commissariat a l'Energie Atomique, Paris (FR)

( * ) Notice: Subject to any disclaimer, the term of this patent is extended or adjusted under 35 U.S.C. 154(b) by 643 days.

(21) Appl. No.: 12/441,225

(22) PCT Filed: Sep. 14, 2007

(86) PCT No.: PCT/FR2007/001501
§ 371 (c)(1),
(2), (4) Date: May 18, 2009

(87) PCT Pub. No.: WO2008/034968
PCT Pub. Date: Mar. 27, 2008

(65) Prior Publication Data
US 2010/0022400 A1 Jan. 28, 2010

(30) Foreign Application Priority Data

Sep. 15, 2006 (FR) ..................... 06 08091

(51) Int. Cl.
*C40B 50/14* (2006.01)
*G01J 3/30* (2006.01)
*C12M 1/00* (2006.01)
*C12M 1/34* (2006.01)
*C12M 3/00* (2006.01)

(52) U.S. Cl.
USPC ........ 506/39; 356/316; 435/283.1; 435/287.2

(58) Field of Classification Search
USPC ................ 506/36; 356/316; 435/283.1, 287.2
See application file for complete search history.

(56) References Cited

U.S. PATENT DOCUMENTS 6,407,811 B1 6/2002 Snyder et al.
6,713,671 B1 * 3/2004 Wang et al. ................... 174/391
(Continued)

FOREIGN PATENT DOCUMENTS
WO WO 02/063284 8/2002

OTHER PUBLICATIONS

Cuzin "DNA chips: a new tool for genetic analysis and diagnostics" Transfusion Clinique et Biologique 8(3):291-296 (2001).
Al-Jeffery et al. "On the use of LIBS and LIFS for rapid detection of Rb traces in blood" Optical Biopsy IV, Robert R. Alfano, Editor, Proceedings of SPIE—The International Society for Optical Engineering 4613:152-161 (2002).

(Continued)

*Primary Examiner* — Robert T. Crow
(74) *Attorney, Agent, or Firm* — Morgan, Lewis & Bockius LLP

(57) ABSTRACT

The present invention relates in particular to a method for the quantitative measurement of biomolecular targets that have been deposited on a biochip (1) of the type with a matrix of probes hybridized by the targets, the matrix comprising a multitude of measurement points (2) each comprising a plurality of probes, characterized in that it comprises the following steps: a) at least one laser beam (18) is focused onto each measurement point, in order to extract therefrom a hot confined plasma comprising a chemical element to be quantified that is present in the targets and optionally in the probes; b) the light emission lines from the plasma are detected and analysed for each measurement point, by measuring the respective intensities of these lines; and then c) the concentration in each measurement point of the element or of a group incorporating it within the targets is determined via a prior calibration of the lines establishing a correlation between the intensities of the lines specific to the element to be quantified and given concentrations of this element.

28 Claims, 16 Drawing Sheets

U.S. PATENT DOCUMENTS

Figure 1:
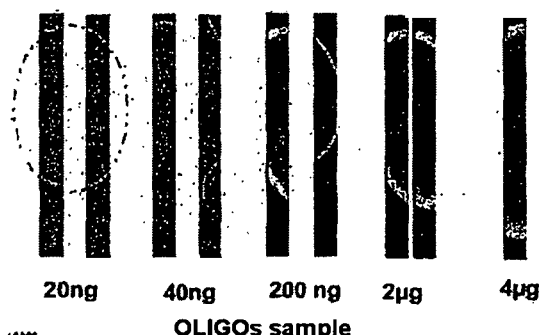

2003/0215872 A1* 11/2003 Clark ............................ 435/7.1
2004/0189990 A1* 9/2004 Shilling ........................ 356/318
2005/0068524 A1* 3/2005 Wu et al. ....................... 356/316
2006/0014191 A1* 1/2006 Lao et al. ......................... 435/6
2006/0105354 A1   5/2006 Remacle et al.

OTHER PUBLICATIONS

Delucia et al. "Laser-induced breakdown spectroscopy (LIBS): a promising versatile chemical sensor technology for hazardous material detection" IEEE Sensors Journal 5(4): 681-689 (2005).

* cited by examiner

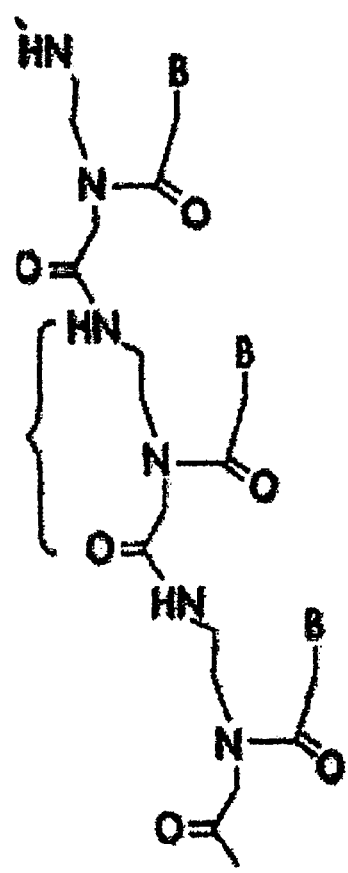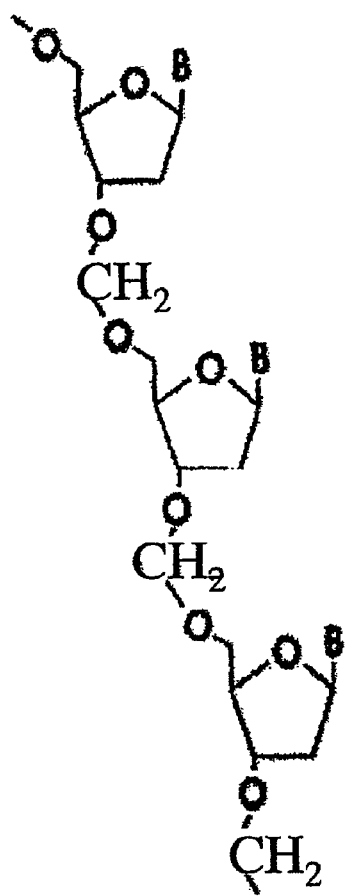
PNA
ERN
Fig. 4
Fig. 5

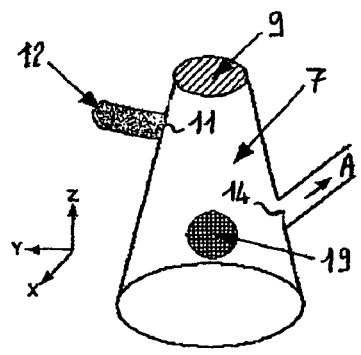 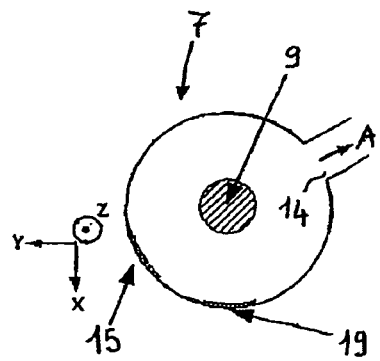
Fig. 8          Fig. 9
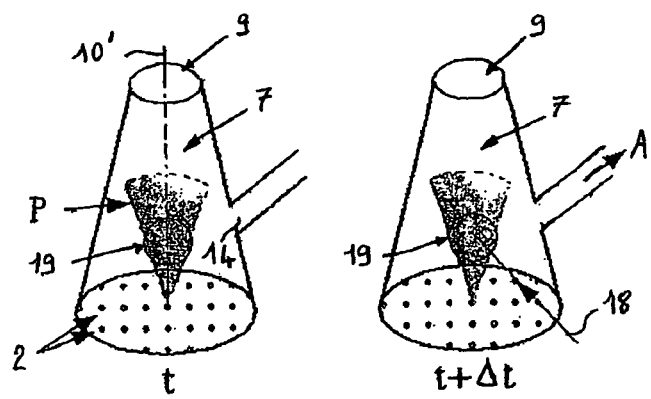
Fig. 10          Fig. 11

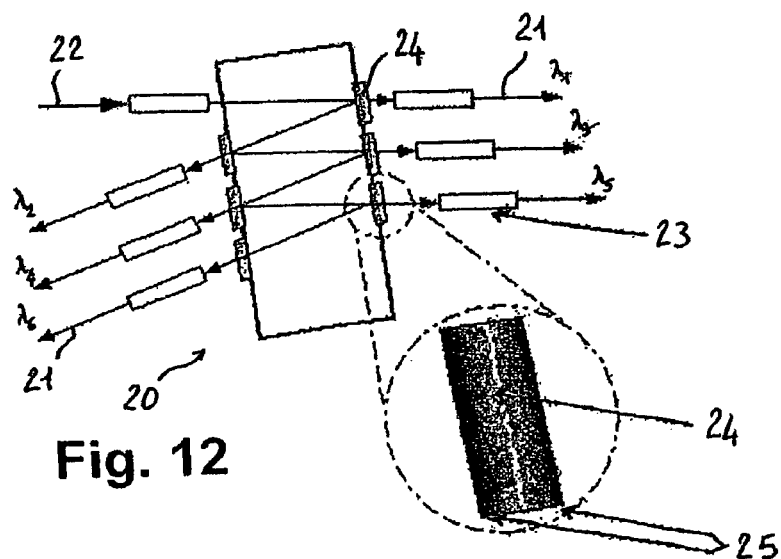
Fig. 12
Fig. 13
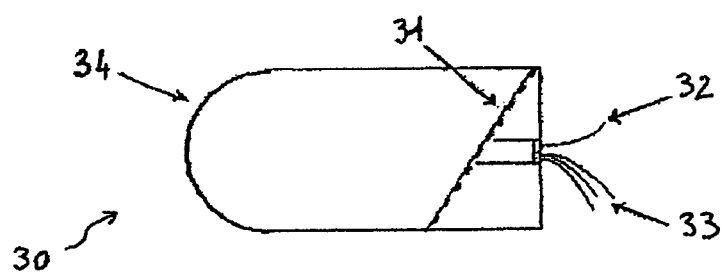
Fig. 14
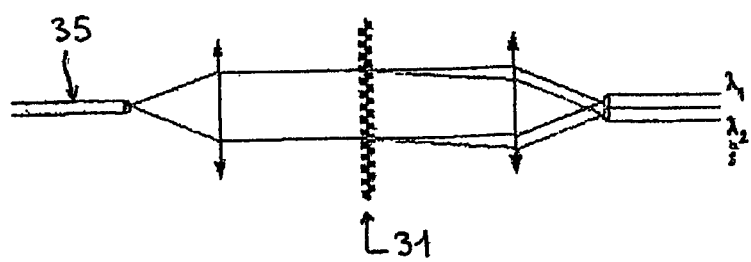
Fig. 15

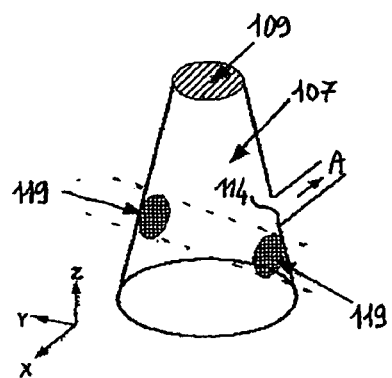 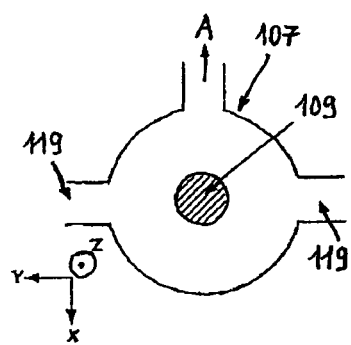
Fig. 18     Fig. 19
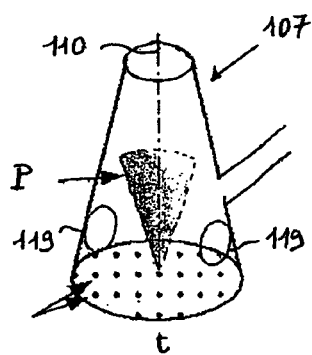 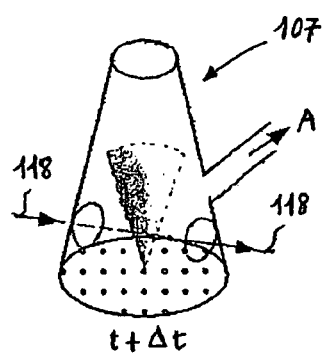
Fig. 20     Fig. 21

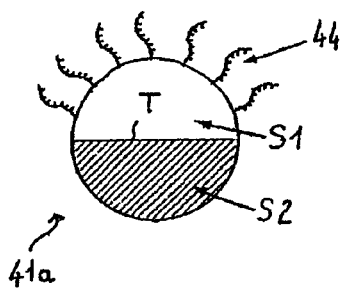
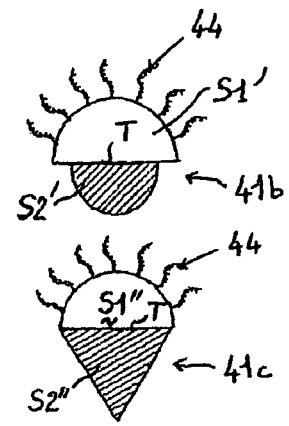
Fig. 22 Fig. 23 Fig. 24
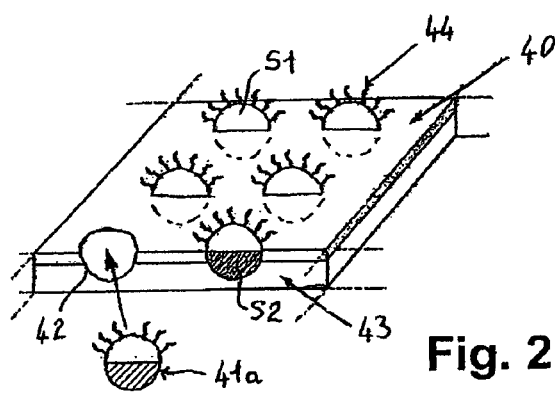
Fig. 25
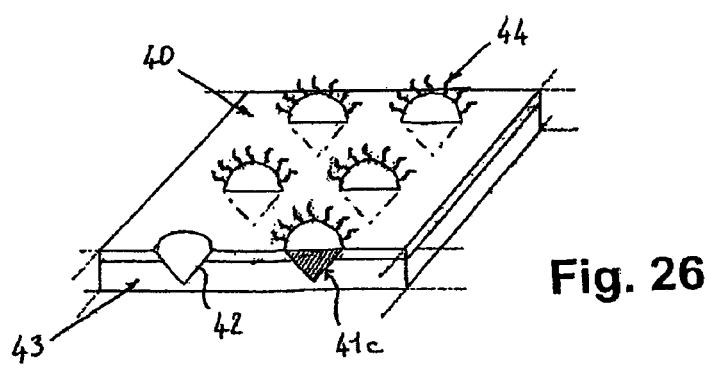
Fig. 26

METHOD FOR THE QUANTITATIVE MEASUREMENT OF BIOMOLECULAR TARGETS DEPOSITED ON A BIOCHIP, AND DEVICE FOR IMPLEMENTING IT

RELATED APPLICATIONS

The present application is a U.S. National Phase Application of International Application PCT/FR2007/001501, filed Sep. 14, 2007, which claims the benefit of French Application No. 0608091, filed Sep. 15, 2006, all of which are herein incorporated by reference in their entirety.

The present invention relates to a method for the quantitative measurement of biomolecular targets that have been deposited on a biochip, and a device for implementing this method. The invention applies in particular to the quantitative measurement of unlabeled nucleic acids that have been hybridized on probes of this biochip.

Biochips represent a major revolution in the molecular biology techniques of the last ten years. By allowing the simultaneous study of the expression level of several hundred, or even several thousand, genes, they make it possible to understand the impact of a disease or of a stress (e.g. resulting from radiation, a pollution or the taking of a medicament) at the level of an individual's complete genome. These techniques are thus becoming increasingly used in modern biology.

Biochips can be divided up into two major groups, comprising microfluidic chips and probe-matrix chips. The latter are organized in matrices of "spots" or measurement points, and they are generally obtained by depositing or by synthesizing, at precise coordinates on a passive support, molecular probes made up of biopolymers such as DNA, proteins or antibodies, for example. These probe-matrix biochips make it possible to identify the targets present in a biological sample when these targets hybridize specifically at each "spot" of probes.

On the one hand, high-complexity biochips (more than 5000 spots) exist for pan-genomic studies and, on the other hand, low- and medium-complexity biochips exist, which are dedicated to a given theme (e.g. therapeutic tests, biological detector).

The current probe-matrix biochip technology has a certain number of major limitations, in particular:

the high steric hindrance of fluorescent labels, which sporadically modifies the recognition between the probes and the targets and thus leads to many measurement artifacts, decreasing experiment reproducibility;

the absence of quantitative measurement, which prohibits comparison of the levels of expression between two different targets; and the high cost of this current technology, both in terms of production and implementation.

This is the reason for which several alternatives to this technology have been recently developed, with in particular:

"RT PCR" technologies in a microfluidic card (Reverse Transcriptase Polymerase Chain Reaction", i.e. a polymerase chain amplification after reverse transcription of a ribonucleic acid to complementary DNA), which make it possible to amplify up to 386 different targets in parallel, with simplification of the implementation and an improvement in the detection, which are, however, penalized by the absence of a quantitative measurement for a real comparison between targets, by the limitation of the number of targets to be analyzed (well below a low-complexity biochip) and by high implementation cost;

biochips on a "nylon" film, based on hybridization of the targets in a large volume and labeling by chemiluminescence, which also provide a simplified implementation and an improved detection, but which are nevertheless penalized by the absence of a quantitative measurement, the large reaction volume required (limiting for analyses of samples of low concentration) and the very high production and implementation costs; and new concepts of biochips without labeling, which are based on the detection of the target by measuring impedance or by surface plasmon resonance (SPR), and which have in particular been described in David F. et al., Bioscience Bioelectron. 2005, in Li C. M. et al., Front Biosci. 2005 or in Macanovic A. et al., Nucleic Acid Research 2004, but which do not allow a quantification of the number of targets, pose a problem for preparing high-density chips and involve, both for the impedance measurement technique and for the SPR technique, measurement artifacts due to the varying sizes and conformation of the targets.

ICP (inductively coupled plasma) spectrometry methods have also been developed, cf. Inchul Yang et al., Analytical Biochemistry (2004), vol. 335, 150-161 or Heinrich F., Arlinghaus et al., Analytical Chemistry (1997), vol. 69, No. 18, 3747-3753, these methods making it possible to quantitatively measure the phosphorus contained in a nucleic acid in order to estimate, for example, the degree of hybridization of said nucleic acid on a "PNA" (peptide nucleic acid) biochip.

However, it appears that the use of mass spectrometry for quantitatively measuring phosphorus using a plasma generated at the surface of a biochip is a slow method (taking typically several hours per 1 $cm^2$ on the biochip), and that the instrumentation required for the implementation thereof is expensive. Furthermore, it should be noted that this "ICP" spectrometry technique is not quantitative since it provides only the crude amount of nucleotides hybridized, without being able to differentiate between the size and the number of the biomolecules.

Patent document US-A-2006/0105354 provides a method for real-time quantification of a multitude of targets formed from labeled nucleic acids and which are bound to the surface of a biochip of the probe-matrix type, comprising in particular the emission of a laser beam for excitation at the surface of the matrix and the measurement of the light emission from hybridized targets in response to this excitation beam.

A major drawback of this method is that it is also not quantitative within the meaning indicated above, and that it requires, in addition, the presence of labeled molecules bound to the target molecules.

An objective of the present invention is to provide a method for the quantitative measurement of biomolecular targets that have been deposited on a biochip of the type with a matrix of probes hybridized by these targets, said matrix comprising a multitude of measurement points or "spots" each comprising a plurality of these probes, which remedies all the abovementioned drawbacks.

To this effect, the method of measurement according to the invention comprises the following steps:

a) at least one laser beam is focused onto each measurement point, in order to extract therefrom a hot confined plasma comprising a chemical element to be quantified that is present in said targets and, optionally, also in said probes, b) the light emission lines from said plasma are detected and analyzed for each measurement point, by measuring the respective intensities of these lines, and then c) the concentration in each measurement point of said element or of a group incorporating it within said targets is determined via a prior calibration of these lines establishing a correlation between the intensities of the lines specific to said element to be quantified and given concentrations of this element.

It will be noted that this correlation between line intensities y and concentrations x is advantageously of linear type (i.e. a relationship of proportionality, within an affinity constant, according to the equation y=ax+b).

It will also be noted that this method according to the invention makes it possible to rapidly and efficiently "scan" (i.e. analyze in one sweep) all the measurement points of the biochip, and to deduce from the abovementioned step c) the number of atoms of said element in each measurement point, in order to deduce therefrom the number of probes that have been hybridized by said targets, all in only a few minutes.

In order to quantify the targets hybridized on the biochip, it will be noted that it is necessary for the size of these targets to be known or calibrated.

According to another characteristic of the invention, prior to step a), each target is advantageously treated in a calibration step (also referred to as standardization by those skilled in the art) in order for its size to be substantially equal to that of each probe, in such a way as to eliminate the nonhybridized parts of the targets. This calibration step is preferably carried out by treating the biochip with an enzyme of nuclease type, such as an exonuclease, which is capable of degrading all the single-stranded nucleic acids that are present on each measurement point so as to preserve only the probe/target double strands.

Preferably, the or each laser beam used in step a) is emitted in the infrared-visible-ultraviolet range according to a pulse lasting between 1 fs and 100 ns, with a frequency of between 10 Hz and 100 kHz and an energy of between 1 mW and 1 kW.

Even more preferably, said or each laser beam is emitted in the ultraviolet range at a wavelength of 266 nm or 193 nm, using, for example, Nd: YAG laser (neodymium-doped yttrium aluminum garnet laser) harmonics, according to a pulse of duration substantially equal to 10 ns.

Also preferably, said or each laser beam has a power density at the surface of each measurement point which is greater than $1\ GW \cdot cm^{-2}$, using a compact laser and focusing lenses, in order to obtain by vaporization a hot plasma with a lifetime of approximately 2 μs.

At these very high densities of energy, it will be noted that a part of the material of each measurement point is ejected from the biochip by the vaporization phenomenon, and this very luminous hot plasma with a very short lifetime is generated. This material ablated in the form of plasma is dissociated into its various atomic and ionic constituents and, at the end of each laser pulse, this plasma rapidly cools. During this period, the atoms and the ions that have been excited emit light radiations which are characteristic thereto, due to their return to lower energy levels.

According to another characteristic of the invention, the plasma generated by said or each beam is confined such that this plasma does not interfere with the other measurement points to be analyzed, and the emission rays from the plasma corresponding to said or to each beam are simultaneously detected.

Advantageously, at least one plasma-activating agent, such as argon, helium, nitrogen or a mixture of these various gases, can be added to the or to each confined plasma.

Also advantageously, it is possible to use a single laser beam which ablates each measurement point according to a 1 μm- to 50 μm-sided surface, and the biochip is then moved relatively with respect to the beam via planar micromovements according to a step of between 1 μm and 100 μm, so as to scan all said measurement points.

As a variant, several laser beams can be simultaneously moved relatively with respect to the biochip, so that these beams ablate all the measurement points.

According to another characteristic of the invention, the laser induced breakdown spectroscopy (LIBS) technique is advantageously used for carrying out steps a) to c), and the laser induced fluorescence (LIF) technique is preferably used, in parallel, for these same steps.

Advantageously, use is made of targets comprising unlabeled nucleic acids, and probes chosen from the group consisting of nucleic acids, peptide nucleic acids (PNAs, see attached FIG. 4 for the chemical formula of a characteristic motif), locked nucleic acids (LNAs) and ribonucleic ethers (ERNs, see attached FIG. 5 for the chemical formula of a characteristic motif) which are transparent for the LIBS technique at a wavelength of 254 nm or of 194 nm.

It will be noted that these molecules, which are resistant to enzymatic digestion by exonucleases, make it possible to protect the parts of the nucleic acid targets that are hybridized with the probes, during a digestion. After digestion, the hybridized nucleic acid targets are thus all known to the operator and equivalent to those of the probes.

It will also be noted that the method for quantitative measurement according to the invention may also be adapted for the study of proteins, using antibodies coupled with nucleic acids (the nucleic acid sequence serving as an anchor and a beacon for recognition of the antibodies).

Advantageously, the phosphorus solely present in these nucleic acid targets is used as element to be quantified for the detection in the plasma, in step b), of atomic and ionic emission lines from phosphorus. As a variant, it is possible to use, for this detection, the phosphorus present both in the nucleic acid targets and in the probes, which in this case also comprise nucleic acids (and therefore phosphoric acid), following a prior step of differentiation between targets and probes.

Also advantageously, the emission lines from phosphorus are detected, in step b), at a wavelength with a value chosen from the group consisting of 138±3 nm, 148±3 nm, 154±3 nm, 167±3 nm, 177±3 nm, 190±3 nm, 193±3 nm, 203±3 nm, 213±3 nm and 253±3 nm.

Even more advantageously, the emission lines from phosphorus are detected, in step b), at a wavelength of 203±3 nm.

It will be noted that the use of probes and targets which are both formed from nucleic acids makes it possible to increase the sensitivity of the detection by increasing the amount of phosphorus measured. However, in certain configurations, it may be advantageous to use PNA probes, in particular when the concentrations of the targets are very low. This is because the very high affinity of PNAs for nucleic acids makes it possible to trap all the oligonucleotide targets present in the medium to be analyzed.

Furthermore, since PNAs are capable of binding spontaneously to a surface of gold via their COOH or NH end, these PNA molecules are particularly advantageous for deposits of probes on a plastic biochip support (e.g. made of "Kapton" polyimide) coated with a layer of gold a few microns thick.

The fact that PNAs do not contain phosphorus, and more generally no atom having a distinctive emission line at 253 nm, at 194 nm or at 203 nm, makes it possible, if absolutely necessary, to carry out the quantification of the oligonucleotide targets directly after the hybridization, without resorting to the abovementioned calibration step in order to degrade the single strands. However, in order for the measurements according to the invention to be absolutely quantitative, this calibration of the targets will have to be carried out.

It will, however, be noted that the method according to the invention could apply to a chemical element to be detected in a plasma other than phosphorus, for example iodine, this example being nonlimiting.

In order to improve the detection limits, it is possible to advantageously:

(i) implement the LIBS technique by performing a double laser pulse of double pulse LIBS type, and/or
(ii) use this LIBS technique in parallel with the LIF technique (i.e. an LIBS-LIF combination).

Via one and/or the other of these two preferred methods (i) and (ii), it is possible in particular to maintain for longer and to amplify the emission lines from phosphorus, and through obtaining a better signal-to-noise ratio, it is possible to thus reduce by a factor at least equal to ten the detection threshold for phosphorus and therefore for the nucleic acids from which it is derived.

Regarding specifically this double laser pulse method (i), it can be carried out with another angle and another beam for the second pulse (power, frequency, wavelength), but also with the same angle and/or with a laser beam of the same nature as that of the first pulse. In fact, given the lifetime of approximately 2 μs of the plasma, the latter is optically analyzable starting from approximately 100 ns after its formation (end of the black body radiation and emergence of the atomic and ionic lines being sought).

This second laser pulse, shortly before its extinction, makes it possible to prolong the lifetime of the plasma and to amplify the emission emitted. A wavelength for which the targeted atom or atoms has (have) a strong absorption or emission, in other words a wavelength characteristic of the atom, is advantageously chosen.

For example, in the case of phosphorus as chemical element to be quantified in the method of the invention, the second-excitation can be carried out at 254 nm, at 193 nm, at 153 nm or at 203 nm, and the detection can be carried out with observation at these same wavelengths (the considerable absorption by air of radiation at 193 nm and radiation at 153 nm can substantially reduce the fluorescence of the plasma at these wavelengths).

It is thus possible to increase the light emission from the ions and/or from the atoms targeted (in the case in point phosphorus), by exciting their specific fluorescence with this second laser pulse.

According to another characteristic of the method according to the invention, the ablation of material of the biochip and the formation of the plasma can be uncoupled. In this case, a first laser pulse ablates a part of the surface of the biochip and ejects it above the latter, and then a second pulse advantageously using a laser of femtoseconds type at a frequency of 100 Hz to 100 kHz creates the plasma and generates the characteristic emission of its constituents. Optionally, a third pulse may subsequently be used in order to excite the fluorescence of the compounds targeted.

The method according to the invention thus makes it possible to efficiently and rapidly detect nucleic acids without labeling the latter, in particular based on the fluorescence of the phosphorus atoms constituting the nucleic acid molecules, after the emission of a plasma. In order to have a truly quantitative measurement of these nucleic acid molecules, the abovementioned calibration of the targets is necessarily carried out via standardization of their respective sizes.

A device according to the invention for implementing the method for quantitative measurement as defined above comprises:

a biochip of the type with a matrix of probes hybridized by biomolecular targets, the matrix comprising a multitude of measurement points or "spots" each comprising a plurality of said probes, a plasma generating and confining unit which comprises means for focusing at least one laser beam onto measurement points in order to extract therefrom a hot plasma containing a chemical element to be quantified, such as phosphorus, present in said targets and, optionally, also in said probes, and means for confining the or each plasma thus extracted, a spectrography unit which is connected to said plasma generating unit and which is suitable for detecting and analyzing light emission lines from the plasma for each measurement point, in such a way that the concentration in each measurement point of said element is determined on the basis of a correlation between the intensities of the lines specific to said element to be quantified and given concentrations of this element.

Advantageously, the targets that hybridize these probes comprise unlabeled nucleic acids, and said probes are chosen from the group consisting of nucleic acids, peptide nucleic acids (PNAs), locked nucleic acids (LNAs) and ribonucleic ethers (ERNs).

According to another characteristic of the invention, the size of each target is advantageously substantially equal to that of each probe subsequent to the abovementioned calibration step, all the targets of each measurement point then being hybridized.

As indicated above, the optical analysis of the plasma generated point by point at the surface of the biochip makes it possible to reconstitute an image at each measurement point of the amount of phosphorus atoms, and therefore of the amount of nucleotides within the nucleic acids forming the hybridized targets. It is thus possible to deduce therefrom the degrees of hybridization of each point or "spot" of the biochip.

It will be noted that, in order to carry out an absolute quantification of the number of oligonucleotides hybridized on each "spot", it is essential that the material constituting the biochip does not contain phosphorus. The applicant has established that a biochip support constituted of polyimide, such as "Kapton", or of this polyimide coated with a layer of gold, is neutral and particularly suitable for carrying out measurements by the LIBS technique at the emission wavelength of between 135 nm and 266 nm. More generally, all types of materials which do not contain phosphorus (e.g. plastic, glass, silica, etc.) and which are compatible with biological materials may be suitable for preparing the biochips according to the invention.

The emission lines from the plasma generated at each measurement point can, for example, be captured by one or more optical acquisition fibers, the free end of which is placed at a distance from the plasma of between 0.5 mm and 10 mm. Owing to their high numerical aperture, the or each acquisition fiber is capped with a set of appropriate lenses (fiber collimator) for correctly injecting the radiations emitted by the plasma.

This device according to the invention thus makes it possible to analyze the surface of a biochip, which is advantageously positioned on a micromovement table (micromovements along two orthogonal directions X and Y). The movements of the table make it possible to scan the entire surface to be analyzed by the or each laser beam with, for example, a step of 10 μm which corresponds to the area ablated at each pulse of the laser.

The optical analysis of the plasma generated point by point at the surface of the biochip makes it possible to reconstitute an image of the amount of phosphorus atoms at each measurement point, which is proportional to the amount of nucleotides. It is therefore possible to deduce therefrom the degrees of hybridization of each measurement point ("spot") on the biochip.

It will be noted that, in order to carry out an absolute quantification of the number of oligonucleotides hybridized on each spot, it is essential that the material constituting the biochip does not contain any phosphorus.

According to another characteristic of the invention, said means for confining the or each plasma extracted comprise at least one arrangement of n plasma chamber(s) ($n \leqq 1$) delimited by an enclosure which surmounts the biochip while being open on the latter, said enclosure being provided with excitation orifices which are each intended to receive an excitation laser beam capable of forming said plasma and having running through it optical fibers for acquisition of the respective emission lines from these plasmas for transmission thereof to the spectrography unit, said or each arrangement of plasma chamber(s) moving relatively with respect to the biochip.

This or these chamber(s) make(s) it possible to confine the plasmas produced and so that there is no interference between the light emitted by these various plasmas in the case of several chambers. As for said enclosure, it may, for example, have a substantially parallelepipedal geometry which is suitable for surrounding the plasma chamber or at least one line of several plasma chambers, and which is formed by a mechanical or laser structuring technique using a powder or a liquid polymer, such as stereolithography, lamination, sintering or photolithography, or else by molding.

As a variant, the plasma chamber(s) may be replaced with a single closed chamber containing the biochip, at least the upper face of which is made of quartz or of any other material that is transparent to the excitation and acquisition wavelengths, this closed chamber being equipped with valves for filling with a plasmagenic gas (e.g. argon/nitrogen) and for flushing of air.

According to a first embodiment of the invention, said plasma generating unit comprises means for emitting a plurality of excitation laser beams and for conveying them, respectively and simultaneously, inside the plasma chambers via said excitation orifices.

According to a first example relating to this first embodiment, these excitation laser beams can be respectively derived from various laser sources. In this case, the excitation orifice of each plasma chamber according to the invention receives an excitation optical fiber which is intended to guide the laser beam corresponding to a given wavelength and which is provided, at its free end, with a first optical lens suitable for causing this beam to converge onto the biochip.

According to a second example relating to this first embodiment, these excitation laser beams can be derived:
from a single laser source which emits an upstream beam at several wavelengths which are superimposed and preferably 0.4 nm to 1 nm apart from one another, and
from a wavelength demultiplexer for separating the upstream beam into downstream beams having, respectively, as many wavelengths as there are excitation optical fibers for carrying them.

According to a second embodiment of the invention, said plasma generating unit comprises means for emitting a single plasma excitation laser beam and for conveying it successively inside said plasma chambers by moving it from one excitation orifice to another via a galvanometer head.

In accordance with said first and second embodiments of the invention, each plasma chamber can be delimited by a lateral surface of revolution, the top of which is provided with one of said excitation orifices, which has on this lateral surface an acquisition orifice receiving said acquisition fiber and which opens out immediately above the biochip via a lower opening of said chamber, so as to confine the plasma extracted therefrom by the corresponding laser beam.

Preferably, the lateral surface of each plasma chamber is cylindrical or conical, becoming wider toward the biochip, between 2 mm and 10 mm in height and opening out at a distance from the latter of between 5 µm and 200 µm, with a diameter for said lower opening which is between 1 mm and 5 mm.

According to another advantageous characteristic of the invention, said arrangement of plasma chambers and said biochip can be respectively mounted mobile along two orthogonal axes X and Y, in such a way that, with each movement of the biochip along the Y axis, said arrangement performs K movements along the X axis, where:
K is defined by the ratio P/l of the distance P between the respective excitation fibers of two adjacent chambers and of the width l along the X axis of the surface ablated at each laser pulse, this ratio being modulated by the shape factor of the ablation after vaporization, and where
the distance P between these two excitation fibers is defined by the equation $P=L/(N-1)$ with $N>1$, L being the width of the biochip and N the number of excitation fibers in said arrangement.

Equally advantageously, the distance P between two adjacent excitation fibers is a multiple of the step between two measurement points on the biochip.

According to another characteristic of the invention, said enclosure can be provided with at least one solenoid suitable for generating therein a magnetic field, so as to increase the lifetime of the or of each plasma and/or to control the shape thereof, and also the selection of the various charged particles.

In addition to this magnetic field, it is also possible to generate an electric field via means that can, for example, consist in using, as biochip support, an electrically conducting material or else a support carrying an electrode with which is associated another electrode carried by said enclosure in order to generate a potential difference.

Preferably, the acquisition optical fiber of each plasma chamber is provided with a second optical lens at its free end emerging in the chamber, and the internal face of said lateral surface is designed so as to locally form a concave mirror capable of optimizing the reflection of the light radiations emitted by the plasma in the direction of said acquisition fiber.

According to another preferential characteristic of the invention, said spectrography unit comprises at least one spectrograph of photomultiplier type. However, it will be noted that a spectrophotometer, a camera of CCD (charge coupled device) or intensified CCD type or else a "wafer" of microchannels could also be used for the detection of the emission lines from the plasma.

Also preferentially, an optical filter which is transparent only to the desired wavelength can be placed between each acquisition optical fiber and the spectrograph.

Also advantageously, said plasma generating unit may also comprise auxiliary means for the emission of a second-excitation laser beam and for the introduction of this beam from one chamber to another, via at least a second-excitation orifice made in the lower part of the lateral surface of each chamber at the height of expansion of the plasma or of expulsion of the material extracted from the biochip, each second-excitation orifice then being made at a position planned so as not to be affected by the acquisition fiber or by said concave mirror.

In relation to said first embodiment of the invention, said auxiliary emission means can advantageously comprise a galvanometer head capable of moving said second-excitation beam from one second-excitation orifice to another and, in this case, each second-excitation orifice may be provided with a third optical lens capable of causing the corresponding second-excitation laser beam to converge at said expansion or expulsion height.

As a variant and in relation to said second embodiment of the invention, each plasma chamber may advantageously have a pair of second-excitation orifices facing one another, such that these pairs of orifices are aligned within said arrangement of chambers for focusing, through this alignment, a second-excitation laser beam emitted by said auxiliary emission means.

According to another characteristic of the invention common to said abovementioned first and second embodiments of the invention, each plasma chamber may also be provided with a gas injection orifice which is made on said lateral surface in immediate proximity to said excitation orifice and which receives a pipe for introducing an inert gas, such as argon or helium, capable of depleting the chamber of oxygen and of activating the plasma at the time it is formed. The procedure can, for example, be carried out under reduced pressure.

According to a preferred exemplary embodiment of the invention, each measurement point may comprise a magnetic or paramagnetic bead, for example made of polystyrene containing particles of cobalt, of nickel or of the oxide thereof, each bead having a color different than that of the rest of the biochip and than that of the other measurement points, such that these beads form optical test objects that can be unequivocally identified by an image capture system with which said spectrography unit is equipped.

According to another characteristic of this preferential example according to the invention, the biochip may comprise a plastic sheet forming a magnetic screen, for example made of polyimide (e.g. "Kapton"), on which are made as many holes as there are beads, and which surmounts a magnetic strip capable of generating, in these holes, a magnetic field with an intensity of between 0.5 T and 5 T.

According to one exemplary embodiment of the invention, each bead is constituted of two half-spheres which are bonded to one another in one of said holes and of which only the lower half-sphere turned toward said magnetic strip has paramagnetic properties, said probes being grafted onto the convex surface of the upper half-sphere which is colored so as to form one of the abovementioned optical test objects.

As a variant, each bead may be constituted of a colored upper half-sphere which is intended to form said optical test object and onto the convex surface of which said probes are grafted, a cone having paramagnetic properties being bonded via its base under the edge of this half-sphere and on the side of said magnetic strip, inside said holes.

It will be noted that the latter bead geometry, which is asymmetrical relative to the median horizontal plane of the bead (parallel to the surface of the biochip), advantageously makes it possible to improve the yield of the method according to the invention.

Figure 2:
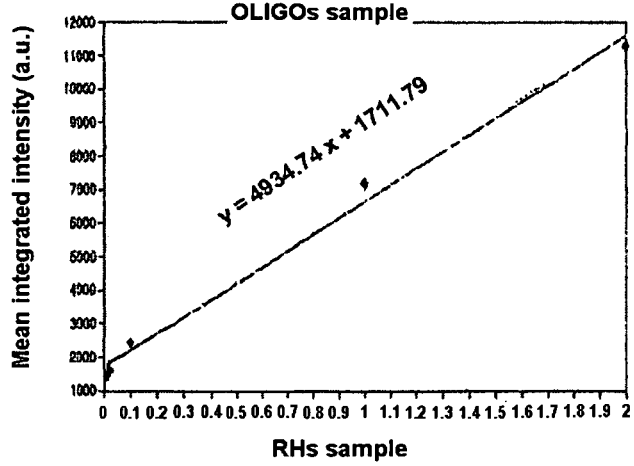
Figure 3:
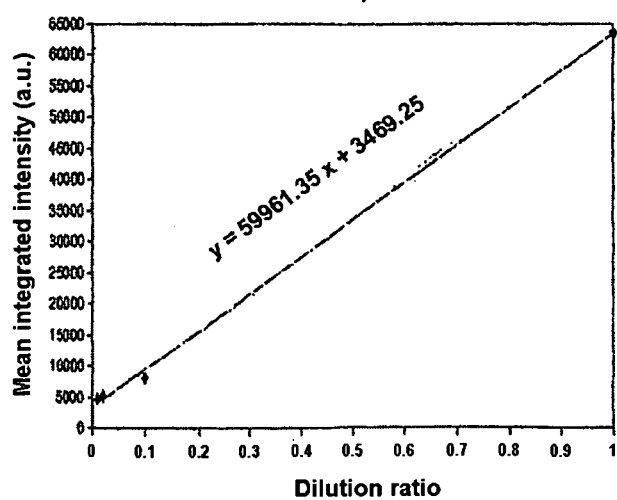
Figure 6:
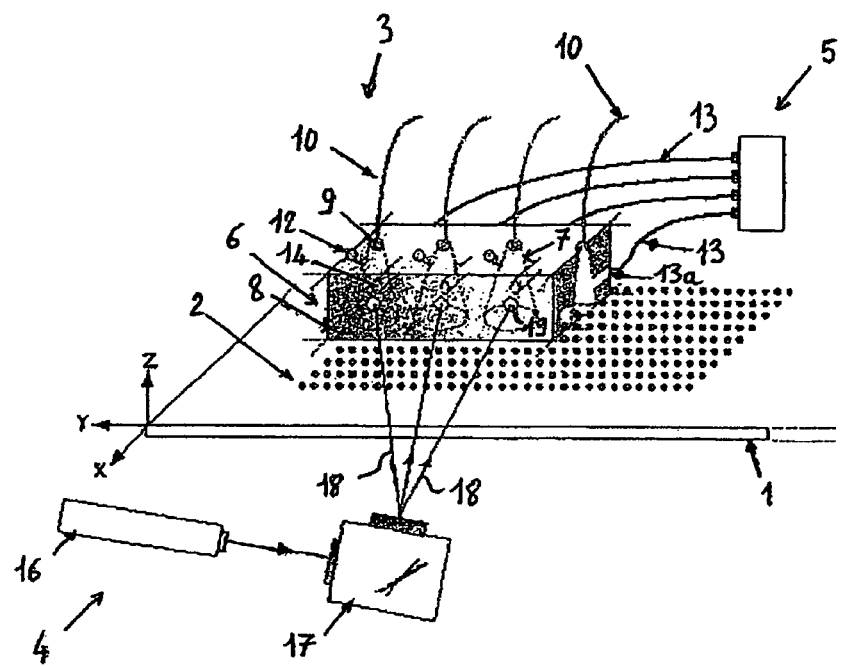
Figure 7:
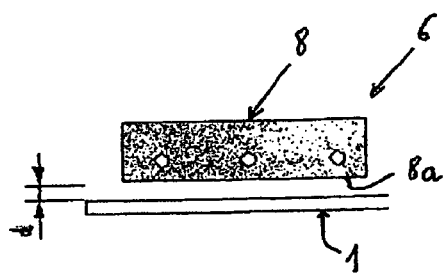
Figure 16:
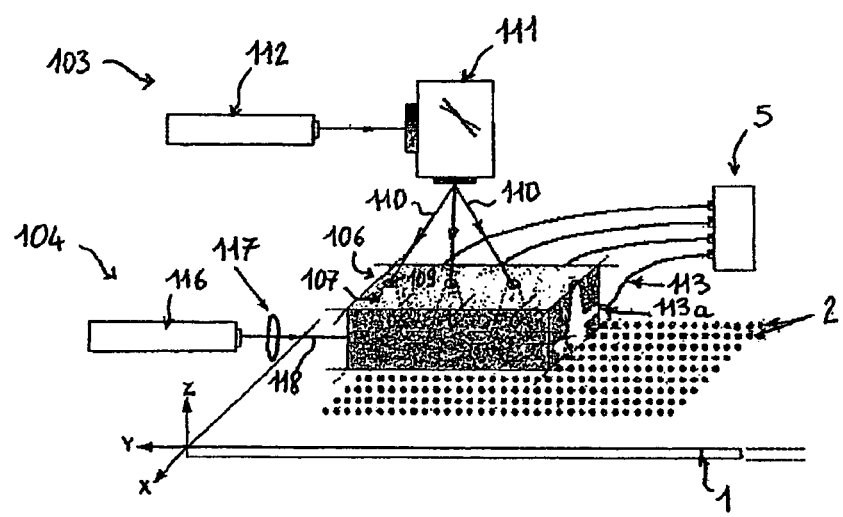
Figure 17:
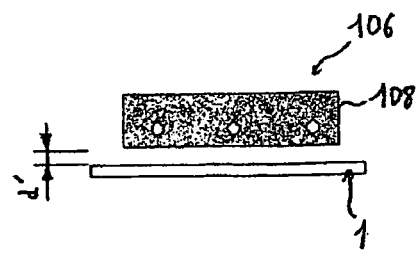
Figure 27:
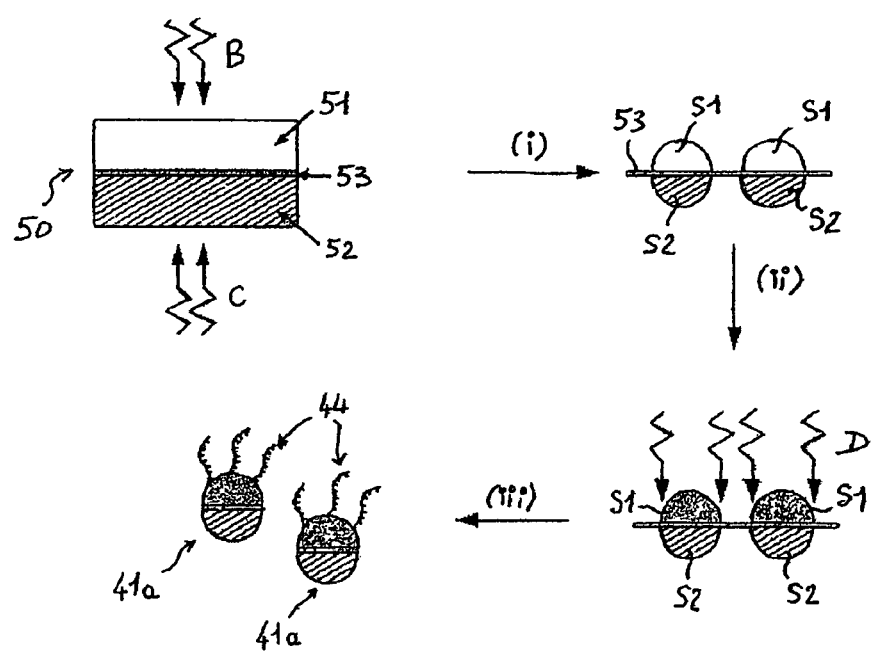
Figure 28:
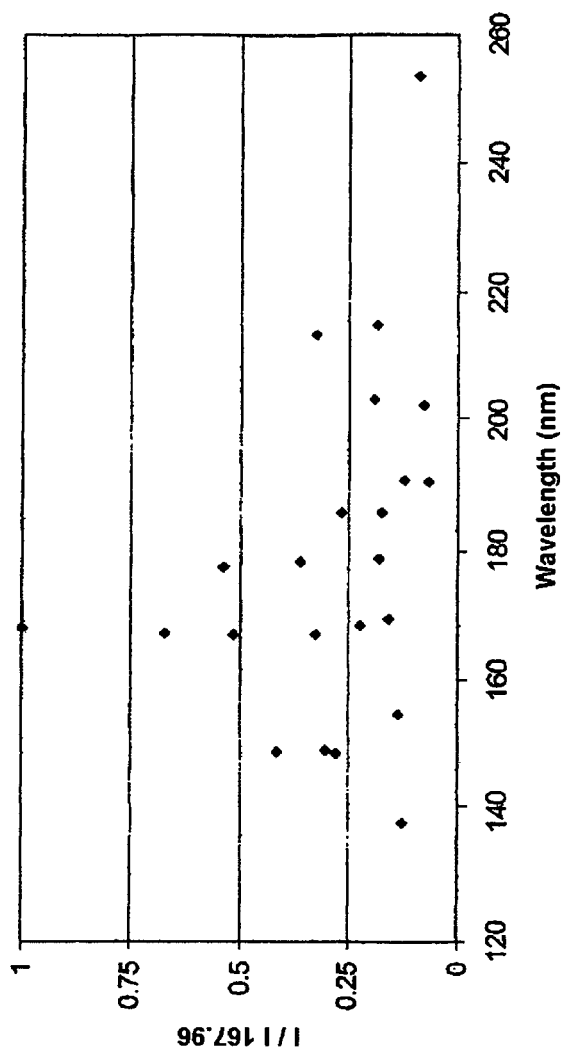
Figure 29:
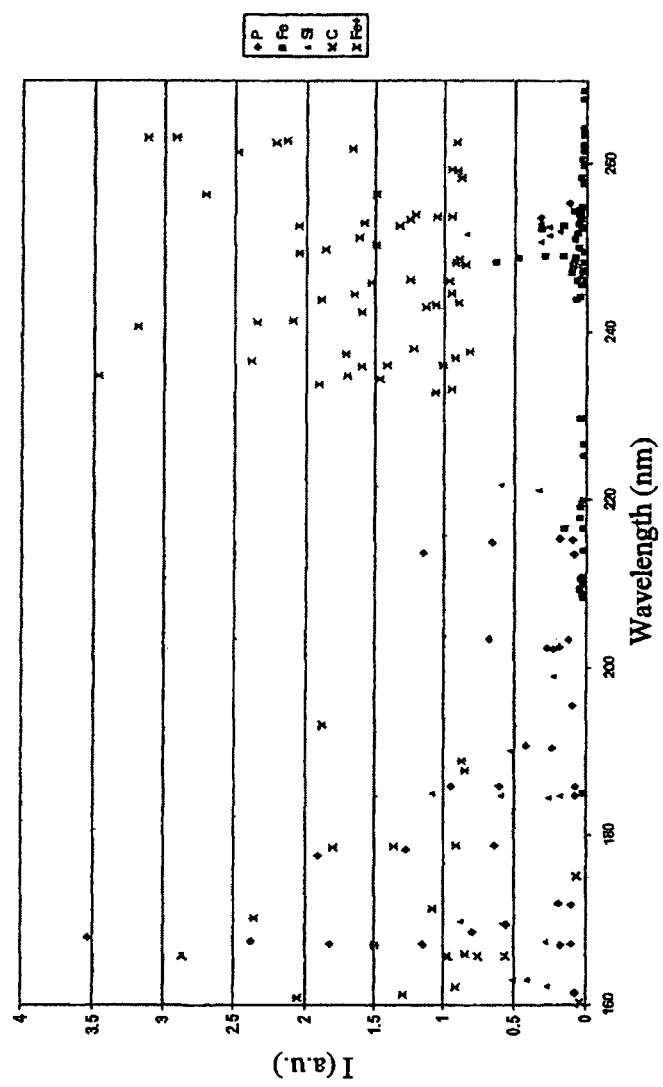
Figure 30:
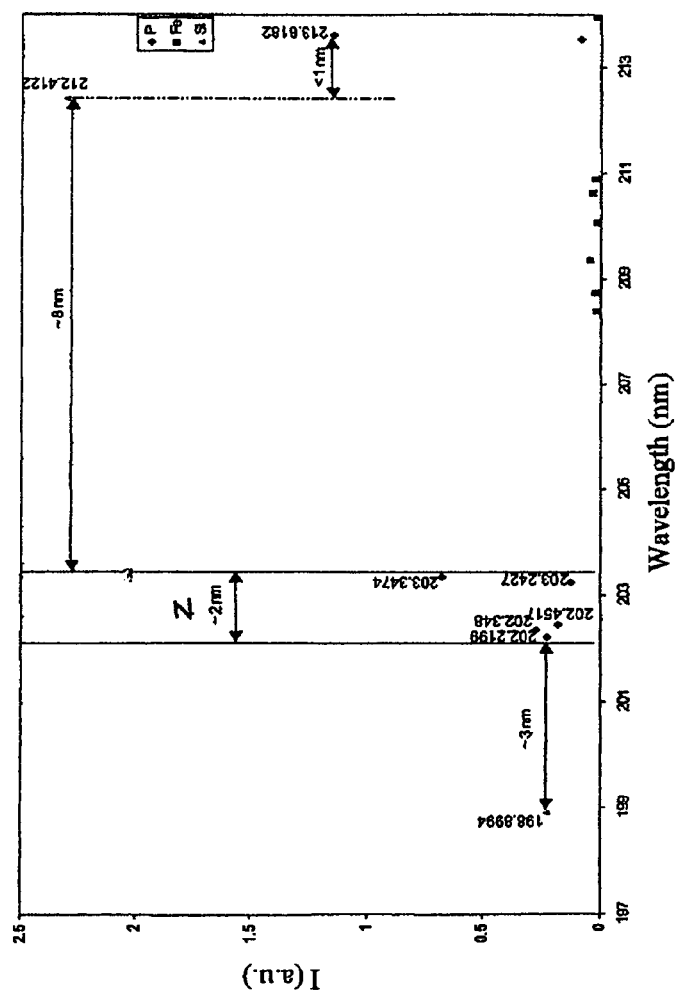
Figure 31:
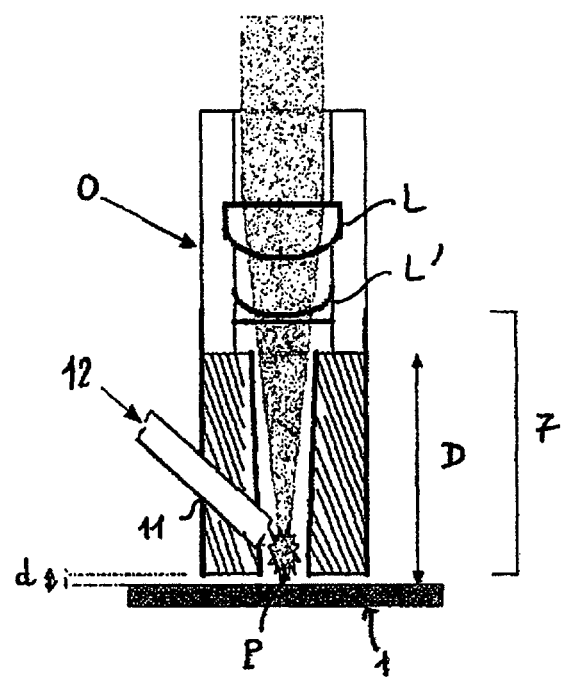
Figure 32:
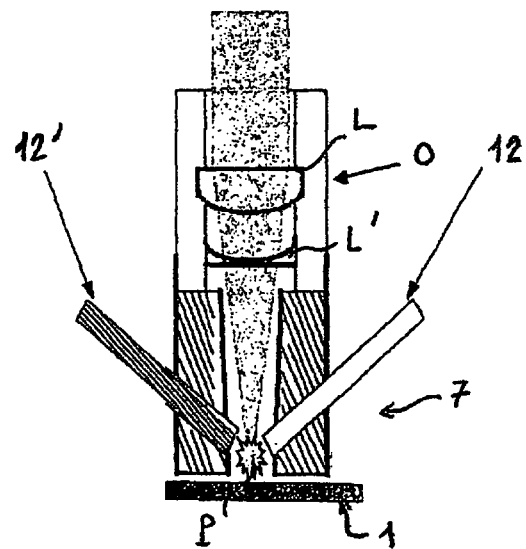
Figure 33:
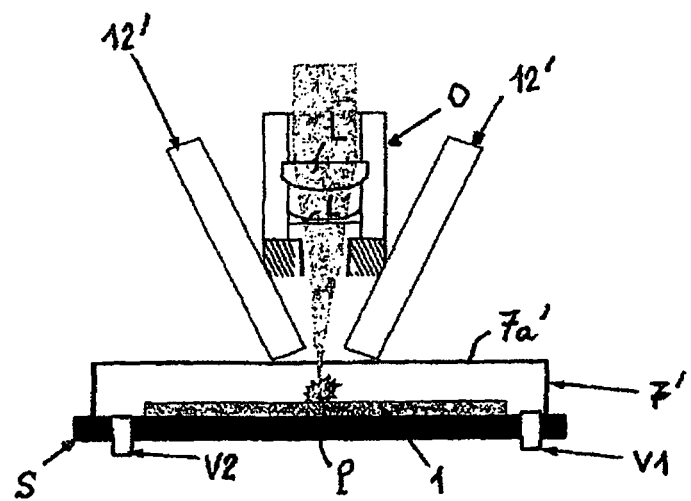
Figure 34:
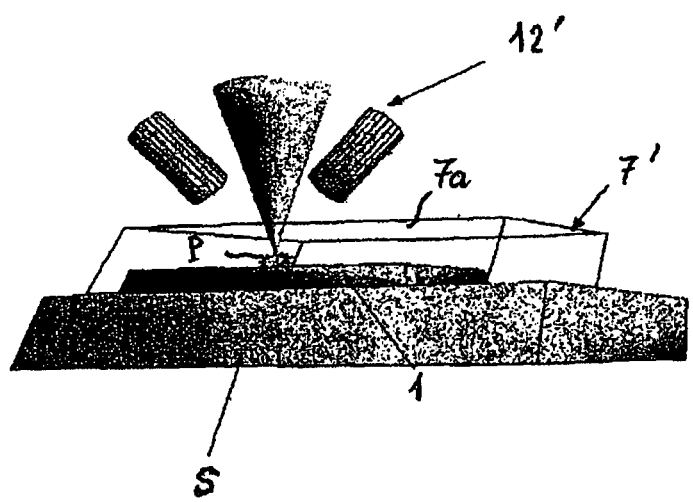
Figure 35:
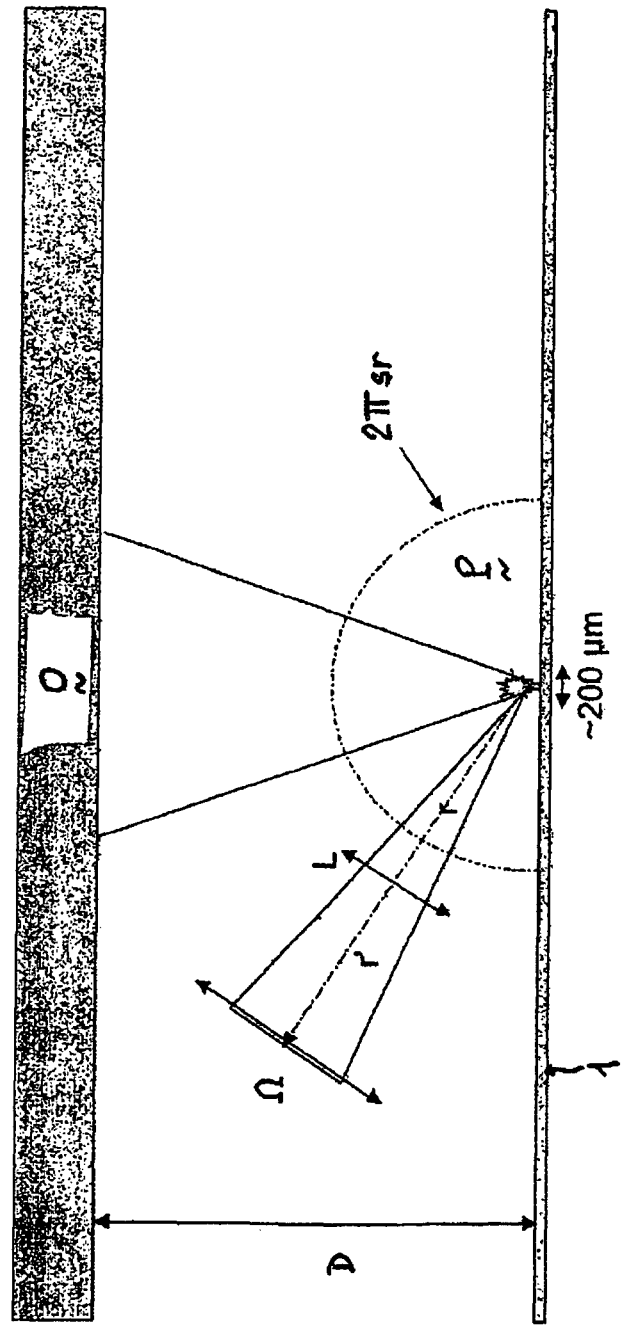
Figure 36:
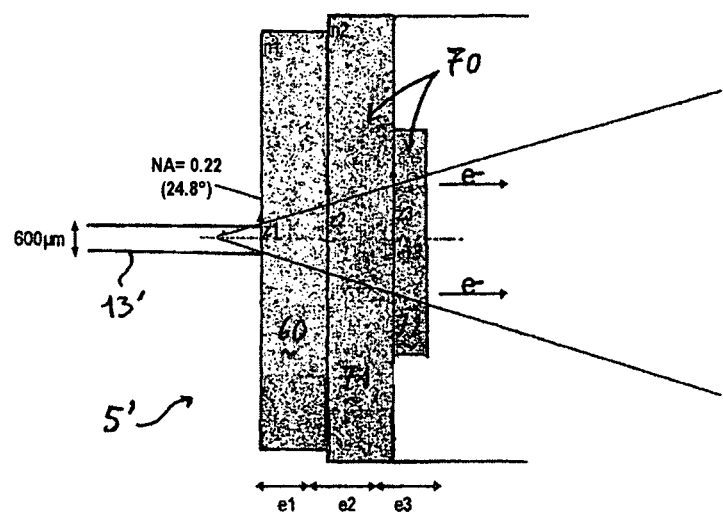
Figure 37:
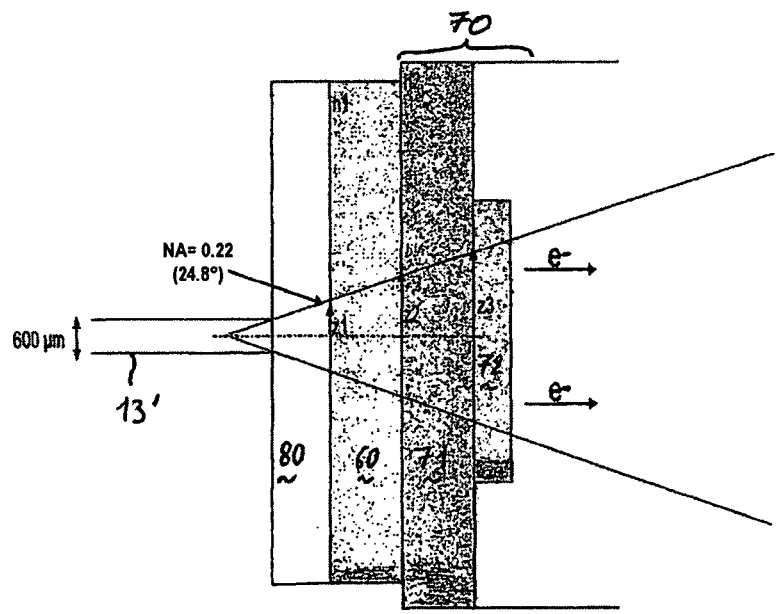

The abovementioned characteristics of the present invention, and also others, will be understood more clearly on reading the following description of several exemplary embodiments of the invention, given by way of nonlimiting illustration, said description being given in relation to the attached drawings, among which:

FIG. 1 represents images illustrating the emission lines from phosphorus in a plasma obtained by the method of the invention, for target samples characterized by various oligonucleotide concentrations (abbreviated to "OLIGOs sample"), FIGS. 2 and 3 are graphs illustrating the relationship of proportionality (within a constant) measured between the intensities of these emission lines and the concentrations or dilution ratios tested, respectively, FIGS. 4 and 5 represent the characteristic sequences of the respective chemical formulae of the PNAs and of the ERNs, that can be used as probes on the probe-matrix biochip according to the invention, FIG. 6 is a partial schematic perspective view of a device for quantitative measurement according to a first embodiment of the invention, FIG. 7 is a schematic side view illustrating the spacing between the arrangement of plasma chambers and the biochip which are included in the device of FIG. 6, FIG. 8 is a schematic perspective view of a plasma chamber included in the arrangement of the device of FIG. 6, FIG. 9 is a view from above of the plasma chamber of FIG. 8, FIGS. 10 and 11 are schematic perspective views illustrating respectively the formation of a plasma at an instant t in the chamber of FIG. 8 and the acquisition, using this chamber, of its emission lines at an instant t+Δt, FIG. 12 is a scheme of the principle of a cascade filtering demultiplexer that can be used according to the invention for breaking down an input laser beam into a plurality of output laser beams, for the guidance thereof in excitation optical fibers of the biochip, FIG. 13 is a medallion illustrating a component of the demultiplexer illustrated in FIG. 12, FIGS. 14 and 15 are two other schemes of the principle of a diffraction-grating multiplexer-demultiplexer, which can also be used as a variant according to the invention of the device of FIGS. 12 and 13, FIG. 16 is a partial schematic perspective view of a device for quantitative measurement according to a second embodiment of the invention corresponding to a variant of FIG. 6, FIG. 17 is a schematic side view illustrating the spacing between the arrangement of plasma chambers in the biochip which are included in the device of FIG. 16, FIG. 18 is a schematic perspective view of a plasma chamber included in the arrangement of the device of FIG. 16, FIG. 19 is a view from above of the plasma chamber of FIG. 18, FIGS. 20 and 21 are schematic perspective views illustrating, respectively, the formation of a plasma at an instant t in the chamber of FIG. 18 and the acquisition, using this chamber, of its emission lines at an instant t+Δt, FIG. 22 is a schematic meridian section view of a bead forming each measurement point of a probe-matrix biochip according to the invention, according to a first example of the invention, FIG. 23 is a schematic meridian section view of a bead forming each measurement point of a probe-matrix biochip according to the invention, according to a second example of the invention, FIG. 24 is a schematic meridian section view of a bead forming each measurement point of a probe-matrix biochip according to the invention, according to a third example of the invention, FIGS. 25 and 26 are two local schematic perspective and partially sectional views of biochips according to the invention incorporating the beads of FIG. 22 and of FIG. 24, respectively, FIG. 27 is a method scheme illustrating the principle steps for producing the beads of a biochip according to FIG. 25, FIG. 28 is a graph illustrating the position and the relative intensity of the atomic lines emitted by phosphorus, relative to its most intense line, as a function of the wavelength, FIG. 29 is a graph illustrating, by way of comparison, the positions and the intensities of the emission lines from the elements P, Fe, $Fe^+$, Si and C in the spectral range 160 nm-260 nm, FIG. 30 is a graph illustrating more precisely the localization and the environment of the study zone selected for the wavelength of the emission lines from phosphorus, in comparison with the elements Fe and Si, FIG. 31 is a partial schematic longitudinal sectional view of a plasma chamber included in a device for quantitative measurement according to the invention, such as that of FIG. 6, illustrating in particular its assembly on the focusing optic and the arrangement of the pipe for supplying plasmagenic gas into this chamber, FIG. 32 is a variant of FIG. 31, illustrating, in addition, for each plasma chamber, the arrangement of optical fibers, FIG. 33 is a variant of FIG. 32, illustrating a plasma chamber constituted of a hermetically closed cell containing the biochip and equipped with valves for filling with plasmagenic gas and for flushing of air, FIG. 34 is a partial perspective view of the arrangement of the hermetically closed cell containing the biochip according to FIG. 33, FIG. 35 illustrates, in terms of solid angle, the manner in which the plasma is emitted in each of the chambers of the device according to the invention, between the objective of the focusing optic and the point of analysis of the biochip that is the site of the emission of lines, and FIGS. 36 and 37 illustrate the characteristics of an example of an optical acquisition system that can be used according to the invention, of optical fiber-interference filter/photomultiplier "CPM" type.

In order to quantify the target nucleic acids which have hybridized on the probes of a probe-matrix biochip, by means of the method of the invention, it is recalled that it is necessary for the size of these targets to be known or calibrated.

In order to obtain this calibration, the biochips are treated, after hybridization, with an enzyme of exonuclease type, such as venom phosphodiesterase 1, exonuclease I, etc., which is capable of degrading all the single-stranded nucleic acids present on the biochip. After this exonuclease treatment and washing, only the probe/target double strands are present on the biochips with targets having exactly the size of the probes (to within the steric hindrance of the exonuclease).

The concentration of phosphorus measured is in proportion to the degree of hybridization, as long as the size and the density of the probes are perfectly calibrated. In fact, as illustrated in the graphs of FIGS. 2 and 3, the intensity of the emission signal measured is linearly correlated with the concentration of an oligonucleotide (tested on a 19 mer) present on a sheet of polyimide known as "Kapton" forming the support of the biochip (see FIG. 1).

The measuring device according to a first embodiment of the invention, which is illustrated in FIGS. 6 to 11, uses in parallel the LIBS and LIF techniques, and it essentially comprises:

a biochip 1 of the type with a matrix of probes hybridized by targets and comprising a multitude of probe spots 2, a plasma generating and confining unit which comprises means 3 and 4 for focusing several laser beams at various points of the biochip 1 simultaneously, in order to extract from each of them a hot plasma containing a chemical element to be quantified, such as phosphorus, which is only present in these targets, and means for confining the or each plasma thus extracted, and a spectrography unit 5 which is connected to the plasma generating and confining unit and which is suitable for detecting and analyzing emission lines from the plasma for each spot 2, such that the concentration in each spot 2 of said element is determined on the basis of a correlation between the intensities of the lines specific to said element and given concentrations of this element.

As illustrated in FIG. 6, the confining means are formed from an arrangement 6 of n plasma chamber(s) 7 ($n \geq 1$), the walls of which are, for example, in the shape of an upright cone becoming wider toward the biochip 1 (cylindrical shapes can also be envisioned). This arrangement 6 is delimited by an enclosure 8, for example of parallelepipedal shape, which surmounts the biochip 1 while being open on the latter and which moves relatively with respect to this biochip 1.

The enclosure 8 is provided with N first-excitation orifices 9 which are respectively made at the tops of the chambers 7 and which are intended to receive N first-excitation optical fibers 10 carrying N first-excitation laser beams 10' (see FIG. 10) and suitable for the wavelength used. An optical lens, such as a liquid lens (not represented), is joined to the free end of each fiber 10, so that the corresponding beam 10' is convergent at the surface of the biochip 1.

When operational, these beams 10' are thus focused onto each spot by the abovementioned focusing means 3, with a view to forming the abovementioned plasma to be analyzed via the LIBS technique or else to ablating only in a first step the material of the biochip 1.

As illustrated in FIG. 7, the lower edge 8a of the enclosure 8 is preferably separated from the biochip 1 by a distance d of between 5 μm and 200 μm. As regards the plasma chambers 7, they each have, for example, a height (along the Z axis) ranging from 2 mm to 10 mm and a lower opening (base of the cone or end of the cylinder) with a diameter that can range from 1 mm to 5 mm.

Each plasma chamber 7 is also provided, on its conical sidewall (see FIG. 8), with a gas injection orifice or pore 11 which is preferably adjacent to the corresponding first-excitation orifice 9 and which receives a pipe 12, such as a tube or a hose, the axis of which is substantially perpendicular to a generatrix of the cone formed by the chamber 7 and which makes it possible to inject a neutral gas such as argon. In fact, in order to limit the absorption of the ultraviolet light emitted by the plasma in the case of targets formed from nucleic acids, the oxygen in the air which is in each plasma chamber 7 is thus flushed out.

Furthermore, N optical fibers for acquisition 13 of the emission lines from these plasmas pass through the enclosure 8 and communicate respectively with the inside of the chambers 7, for transmission to the spectrography unit 5 of the line spectra specific to each chamber 7 (see arrow A in FIGS. 8, 9 and 11). Each of the acquisition fibers 13 is received in an acquisition orifice 14 made in the sidewall of a chamber 7, and the free end of each fiber 13 is capped with an optical lens 13a suitable for injecting the light emitted by the plasma into this fiber 13.

In addition, the internal conical (or cylindrical) face of the wall of each chamber 7 located opposite the acquisition orifice 14 is polished and metallized, so as to form a concave mirror 15 (like an integration sphere, see FIG. 9) capable of reflecting a maximum amount of light toward the acquisition fiber 13.

The other focusing means 4, which are included in the plasma generating and confining unit, are, for example, intended to implement the abovementioned LIF technique, in parallel to the LIBS technique. These means 4, which constitute auxiliary second-excitation means, can also serve to generate the plasma in each chamber 7, after the ablation carried out by the focusing means 3.

To this end, these focusing means 4 comprise a laser head 16 associated downstream with a galvanometer head 17, for focusing, according to varying angles, a single second-excitation laser beam 18 through a second-excitation hole or slit 19 made both in the enclosure 8 and in the sidewall of each chamber 7 (see FIGS. 8 and 9). Each hole or slit 19 is made at the anticipated height of expansion of the plasma or else at the height of expulsion of the ablated material of the biochip 1, and at a "blind" angle with respect to the corresponding acquisition fiber 13 or with respect to the mirror 15.

Opposite each hole or slit 19, it is possible to place an optical lens (not illustrated) which causes the laser beam 18 to converge at the level of formation of the plasma or of the ejected material (this plasma is symbolized by the reference P in FIG. 10). This lens may optionally rest on small magnetic jacks constituted of electromagnets which make it possible to focus the lens.

The laser beam 18 is moved from one second-excitation hole or slit 19 to the other by means of a set of mirrors mounted on galvanometric motors which form the abovementioned galvanometer head 17. This assembly makes it possible to advance or delay, by the desired amount of time, the second excitation pulse 18 with respect to the pulse of the first-excitation beam 10' carried by each optical fiber 10.

As regards the spectrography unit 5, it comprises a detector which is preferably a photomultiplier (abbreviated to PM), a spectrophotometer, a CCD or intensified CCD camera or a "wafer" of microchannels, for example. An optical filter which selects only the desired wavelength can be intercalated between each acquisition optical fiber 13 and the detector, in order to inject the light into the latter. Furthermore, a suitable lens may be attached at the output of each optical fiber 13.

This device according to FIGS. 6 to 11 makes it possible to scan the entire surface of the biochip 1 more rapidly than with the prior art devices. The analysis time during this scanning will be inversely proportional to the number of excitation beams 10' used.

The various first-excitation beams 10' carried by the N fibers 10 can be obtained from various laser sources. However, an alternative consists in using a single source producing a beam constituted of the superimposition of several wavelengths that are close to one another (typically 0.4 nm to 1 nm apart from one another), and then breaking down the beam using a wavelength demultiplexer (Wavelength Division Multiplexing or abbreviated to WDM), in order to inject each wavelength into a single fiber 10. FIGS. 12 to 15 illustrate this variant according to the invention for obtaining the abovementioned N first-excitation beams.

More specifically, to this effect, use may be made of a cascade filtering demultiplexer 20, such as that illustrated schematically in FIG. 12, which shows the N=6 downstream beams 21 of respective wavelengths $\lambda_1$ to $\lambda_6$ which are obtained from the upstream beam 22. These downstream beams 21 are respectively derived from collimators 23 which are each constituted, for example, of a gradient index lens. As illustrated in the medallion of FIG. 13, each of the six cavities 24 which comprises the demultiplexer 20 is surrounded laterally by multilayer dielectric reflectors 25.

It will be noted that this upstream beam 22 must be of sufficient energy (since taking into account the possible losses associated with the assembly), such that all the wavelengths used produce a beam that has sufficient energy to bring about the partial vaporization of the surface of the biochip 1 and the formation of a plasma. Where appropriate, the plasma will be produced by a second laser pulse in the expelled material, by means of another beam having a wavelength suitable for inducing the emission from the atoms expelled, and more particularly those of phosphorus, as previously explained.

As a variant, a diffraction grating multiplexer-demultiplexer, such as that illustrated in FIGS. 14 and 15, may be used.

The multiplexer-demultiplexer 30 of FIG. 14 comprises a diffraction grating 31 and, at its end which is opposite that provided with the input optical fiber 32 and the output optical fibers 33, a spherical mirror 34 capable of reflecting the incident beam so as to generate the beams respectively carried by the output fibers 33. FIG. 15 illustrates, for its part, the multiplex 35 provided upstream of the optical system incorporating this diffraction grating 31.

With regard to the relative movements to be carried out between the arrangement 6 of plasma chambers 7 and the biochip 1, this arrangement 6 can, for example, be placed on a structure that moves along an axis X (see FIG. 6). The movements along this X-axis are provided by a stepping motor, a system of magnets or electromagnets, a galvanometer system or any other system for providing a precise movement along the X-axis (in certain situations, the X-axis may be circular with a constant radius).

The biochip 1 to be analyzed moves, for its part, along an axis Y perpendicular to the direction of the X-axis, and the movements on this Y-axis are provided by systems equivalent to those described above for the X-axis. The movements along X and along Y are defined by the height Z along Y and the width I along X of the surface probed at each laser pulse. If this surface probed at each pulse is not rectangular in section, the movements along X and along Y will have to be reduced to Z/2 and I/2, in order to make it possible to ablate the entire surface of the areas traveled.

At each movement of the biochip 1 along the Y-axis, the arrangement 6 of plasma chambers 7 makes K movements along the X-axis, the number K being defined by the distance P between the excitation fibers 10 of two consecutive plasma chambers 7 and by the width I along X of the surface ablated at each laser pulse, in such a way that K is equal to P/I (modulated by the shape factor of the ablation after vaporization).

The abovementioned distance P between two consecutive excitation fibers 10 is defined by the width L of the biochip 1 to be analyzed and the number N of excitation fibers 10 of the arrangement 6, in such a way that P is equal to L/(N−1) if N>1.

The same reasoning can be held for the movements along the Y-axis, if the arrangement 6 is constituted of several lines of plasma chambers 7 that are joined. All the movements in the X and Y directions can be provided by a motorized platform.

In order to decrease the surface to be ablated so as to carry out the analysis of a biochip 1, the chosen gap between two consecutive excitation fibers 10 is advantageously a multiple of the step of the probe spots 2 on the biochip 1. In fact, the matrices of probe spots 2 forming the biochips 1 according to the invention are such that these matrices have a spacing of one constant step over large regions of the biochip 1 (typically several cm²). By producing an arrangement 6 of plasma chambers 7 taking into account this step, it becomes possible to ablate only the regions onto which probes have been grafted.

Similarly, the resolution of the ablation and the values of the movements along X and along Y between two ablations are advantageously suitable for the region of the biochip 1 which is examined. All the movements along the X- and Y-axes can, for example, be provided by a single micromovement platform on which the biochip 1 is placed, the plasma chambers 7 remaining fixed.

The measuring device according to a second embodiment of the invention, which is illustrated in FIGS. 16 to 21, also uses the LIBS and LIF techniques in parallel, and it differs essentially from the device according to the first embodiment of the invention which has just been described with reference to FIGS. 6 to 11, in the following way.

Firstly, the arrangement 106 of plasma chambers 107 according to the second embodiment is not provided with excitation fibers, due to the fact that it is the first-excitation orifices 109 at the top of each plasma chamber 107 which serve as input points for a single excitation laser beam 110 delivered by focusing means 103. An optical lens (not illustrated) which causes the laser beam 110 to converge at the surface of the biochip 1 to be analyzed is advantageously placed at each orifice 109, it being possible for this lens to optionally rest on small magnetic jacks constituted of electromagnets which make it possible to focus the lens.

As illustrated in FIG. 17, the enclosure 108 is preferably separated from the biochip 1 by a distance of between 50 µm and 100 µm.

The movement of the laser beam 110 from one excitation orifice 109 to the other along the arrangement 106 of chambers 107 is provided by a set of mirrors mounted on galvanometric motors, thus forming a galvanometer head 111 provided for downstream of a laser head 112. This system of galvanometric mirrors is defined in such a way that the laser beam 110 is always perpendicular to the surface of the biochip 1, in the area thereof to be analyzed. This involves the use of a mirror having a length in the region of the sum of the length and the amplitude of movements of the arrangement 106, and of two other mirrors of smaller size.

Another embodiment of this galvanometer head 111 may consist in using, in addition to the two mirrors that only have a rotational movement, a mirror that has not only a rotational movement but also a translational movement, as illustrated in FIG. 16. Use is preferably made of a galvanometer head 111 with a telecentric objective providing a working field for which the excitation beam 110 remains perpendicular to the surface to be analyzed.

It will be noted that many possibilities exist for ensuring the perpendicularity of the excitation beam 110 to the biochip 1, this constraint making it possible to correctly synchronize the movement of the arrangement 106 of chambers 107 and of the beam 110, for reconstituting the image.

Secondly, the auxiliary second-excitation means 104 comprise a laser head 116 associated with a focusing lens 117, for the second emission of a single focused laser beam 118 according to the LIF technique. To this effect, two second-excitation holes or slits 119 are provided opposite one another on the sidewall (conical or cylindrical) of each plasma chamber 107, facing one another at the anticipated height of expansion of the plasma or at the height of expulsion of the ablated material, and always at a "blind" angle with respect to each of the N acquisition fibers 113 (each provided with the lens 113a analogous to the lens 13a in proximity to the corresponding acquisition orifice 114 of the chamber 107) or with respect to the abovementioned concave mirror (see FIGS. 18, 20 and 21).

As illustrated in FIG. 16, all the chambers of the arrangement 106 are connected by an imaginary straight line passing through the N pairs of second-excitation holes or slits 119 of the n chambers 107.

It is thus possible to excite, via these auxiliary second-excitation means 104, all the plasmas generated by the single laser beam 110.

Example of Implementation of the Method According to the Invention and of Fabrication of a Biochip Used in this Method:

It should be noted, beforehand, that the excitation fiber 10 provided at the top of each plasma chamber 7 of the device according to the first embodiment of the invention can be doubled or even tripled with one or two additional fibers so as, on the one hand, to allow the capture of the image of the surface of the biochip 1 (in "RGB" mode, i.e. red green blue) by a video camera or digital photographic device and so as, on the other hand, to provide lighting of this surface with a white light. This device according to the invention thus makes it possible to produce a color or black and white image of the surface of the biochip 1.

As a result, it is possible to pinpoint the position of the probes, provided that they are grafted onto optical test objects that have a color different than that of the background of the biochip 1. The ablation will be triggered only when the plasma chamber 7, 107 surmounts one of these optical test objects. In this configuration, a color code can be established by mixing the three basic colors of the RGB code on the 3 times 256 possible levels (levels normally managed by a video camera or by a digital photographic device). This therefore provides 16 777 216 possible colors for these optical test objects, and makes it possible to assign an optical test object of different color to each target spot 2.

In order to produce these optical test objects of different colors, color printer pigments, which do not contain phosphorus (i.e. cyan, magenta, yellow, abbreviated to CMY), can be used. Similarly, it is possible to use a printer having 16 million colors for printing an array of optical test objects of different colors on the biochip 1 (the printer performs the conversion RGB into a mixture of pigments).

Each target spot 2 is then grafted onto an optical test object having a single color, allowing its unequivocal identification at the time the biochip 1 is read. By using this method of optical test objects, it is possible to analyze a biochip 1 in which the probe spot distributions are random in the matrix forming said biochip.

In order to do this, the following are advantageously implemented, in combination according to the present invention:
  the method for analyzing nucleic acids in suspension which is described in the international patent application filed on Feb. 24, 2006 by the applicant under No. PCT/FR2006/00428, and
  the method for the fabrication of an organized array of probes bound to a support by magnetic coupling by means of a fixing vector, which is described in international patent application WO-A-02/43855 in the name of the applicant.

More specifically, a large number of copies of each biomolecular probe is grafted onto a magnetic or paramagnetic bead of a given and a single color. It may, for example, be a calibrated polystyrene bead containing particles of cobalt, of nickel or of an oxide thereof.

The particles are painted or dyed, for example, in their mass with a mixture of pigments, as described for the optical test objects. These particles are then mixed stoichiometrically, so as to obtain a stoichiometric mixture of different probes in which each one is capable of hybridizing to a nucleic sequence present in a mixture of targets to be analyzed.

The probes and the targets are mixed, each type of probe hybridizing to the complementary targets and saturating them. The particles and the probe/target complexes are isolated, washed and then resolubilized.

With reference to FIGS. 22 to 26, a sheet 40, for example based on a polyimide such as Kapton, 1 μm to 10 μm thick (preferably equal to the diameter of each bead 41a, 41b or 41c) is pierced with a multitude of holes 42 of diameter equal to that of the beads 41a, 41b, 41c so as to form a matrix of holes 42 (ideally, there are as many holes 42 as there are beads 41a, 41b, 41c). This "Kapton" sheet 40 is placed or alternatively bonded onto a magnetic strip 43, the sides of which are a few centimeters (ideally, 2.5 cm×7.6 cm). The strip 43 is advantageously constituted of a polymer or of a resin containing magnetized particles, and the magnetic field generated by the strip 43 is of the order of 0.5 T to 5 T. The sheet 40 forms a magnetic screen over its areas covering the strip 43, whereas it leaves the magnetic field free at the holes 42.

According to the exemplary embodiment of FIG. 22 in relation to FIG. 25, each bead 41a is constituted of two identical half-spheres S1 and S2 which are bonded to one another, via their respective edges T (i.e. flat surfaces), in one of these holes 42, and only the low half-sphere S2 of which, turned toward the magnetized strip 43, has paramagnetic properties, since it is, for example, made of a polymer or a resin containing paramagnetic particles.

Also visible in FIGS. 22 to 26 are the biological probes 44 grafted onto the convex surface of the upper half-sphere S1, which is colored so as to form the abovementioned optical test object.

In the variant of FIG. 23, the lower half-sphere S2' has a diameter smaller than that of the colored upper half-sphere S1', onto which the probes 44 are grafted, and it is also assembled by bonding to said upper half-sphere in a centered manner, via the respective edges T of the half-spheres S1' and S2', thus forming each bead 41b.

In the other variant illustrated in FIGS. 24 and 26, each bead 41c is constituted of a colored upper half-sphere S1", onto the convex surface of which the probes 44 are grafted, a cone S2" with paramagnetic properties being bonded, via its base, under the edge T of this half-sphere S1" and facing the magnetic strip 43, inside the holes 42.

It will be noted that this asymmetric geometry of the bead 41c makes it possible to improve the yield of the method and, in addition, to insert such beads 41c more readily into the holes 42 of the sheet 40, which are also provided in a conical shape.

As indicated above, the upper half-sphere S1, S1', S1" of each of these beads 41a, 41b, 41c is advantageously constituted of a painted or colored plastic, such as polystyrene (or of any other biocompatible material which does not contain phosphorus).

After having assembled the "Kapton" sheet 40 on the magnetic strip 43, the bead/probe/target complexes are deposited at the surface of this sheet 40 covering this strip 43. A stylus, the tip of which is supplied with a magnetic field that is lower than the field of the strip 43 (typically from 0.5 T to 1.5 T, via a static magnet or an electromagnet), is then moved over the sheet 40, at a distance which represents substantially three quarters of the average diameter of the beads 41a, 41b, 41c. The latter are attracted by this stylus, and move at the surface of the sheet 40, due to the fact that the magnetic field through the sheet 40 is weaker than that of the stylus. However, as soon as the stylus passes in proximity to a hole 42 of the sheet 40, a bead 41a, 41b, 41c is captured by the magnetic field, due to the fact that the latter is stronger in this hole 42. Owing to the size of the holes 42 and to the competition between the magnetic fields, a single bead 41a, 41b, 41c will be captured per hole 42. Once all the beads 41a, 41b, 41c have been captured, the strip 43 can be removed, leaving the beads 41a, 41b, 41c on the sheet 40.

The magnetic strip 43 and/or the "Kapton" sheet 40 is (are) subsequently analyzed by the measuring device according to the invention described above. The color of each bead 41a, 41b, 41c is determined by virtue of the image capturing system, thereby making it possible to determine the nature of the probe 44. The amount of probes 44 attached to each bead 41a, 41b, 41c is determined by quantifying the phosphorus, after ablation of material and analysis of the emission lines from a hot plasma generated by this ablation.

As illustrated in FIG. 27, the fabrication of the magnetic polar beads 41a can be carried out by laser machining (see arrows B and C) of a plate 50 constituted of two sheets or films 51 and 52 made of different materials which are respectively constituted of polystyrene and of a paramagnetic resin and which are bonded together via an adhesive layer 53. For example, it is possible to use two sheets 51 and 52 based on a polymer known as "Vacrel", of which only the lower sheet 52 contains nickel or cobalt nanoparticles.

In a first step (i), pairs of half-spheres S1 and S2 bonded together are thus obtained through this laser machining, these pairs being connected to one another via the adhesive layer 53.

In a second step (ii), the upper half-spheres S1 are colored, when the material forming them is not already colored.

In a third step (iii), these pairs of half-spheres S1 and S2 are separated by means of a further laser machining (arrows D), for individualizing the corresponding beads 41a and grafting the probes 44.

The beads 41a are thus polymerized in the mass of the films 51 and 52, by focusing of a laser beam. The final structure of the beads 41a can be obtained by means of masks or of a grid placed at the surface of the films 51 and 52, in order to obtain each pair of half-spheres S1 and S2 bonded together. These beads 41a are released by digestion of the nonpolymerized parts of the films, via sodium hydroxide.

Another alternative for preparing these magnetic polar beads consists in producing them using two different photosensitive resins and one or two laser beams, in order to perform stereophotography. A first magnetically neutral resin is used for the synthesis of the first part (e.g. half-sphere S1) of the bead 41a, and a second resin containing paramagnetic cobalt or nickel particles is used for the synthesis of the second part (e.g. half-sphere S2).

With reference to FIG. 28 relating to the atomic lines of phosphorus, this element has an emission spectrum exhibiting intense lines in the UV range and the extreme UV range. At a temperature of 13 000 K, the most intense phosphorus line is at 167.96 nm. Classified in order of relative intensity ($I/I_{167.96}$), the 24 most intense phosphorus lines are listed in table 1 below and in corresponding FIG. 28:

TABLE 1

| λ (nm) | $I/I_{167.96}$ |
|---|---|
| 167.9697 | 1 |
| 167.4595 | 0.670 |
| 177.4949 | 0.538 |

TABLE 1-continued

| λ (nm) | I/I₁₆₇.₉₆ |
|---|---|
| 167.2476 | 0.514 |
| 149.1365 | 0.415 |
| 178.2829 | 0.360 |
| 167.1671 | 0.327 |
| 213.6182 | 0.325 |
| 167.1068 | 0.324 |
| 149.3009 | 0.302 |
| 148.8022 | 0.278 |
| 185.941 | 0.268 |
| 168.5975 | 0.224 |
| 203.3474 | 0.191 |
| 214.9142 | 0.186 |
| 178.7648 | 0.181 |
| 185.8901 | 0.172 |
| 169.4031 | 0.157 |
| 154.8461 | 0.135 |
| 138.1476 | 0.125 |
| 190.7661 | 0.120 |
| 253.5612 | 0.092 |
| 202.348 | 0.077 |
| 190.5478 | 0.067 |

It should be noted that the calculation of the intensity of the lines is based on the following equation:

$$I_{ij} = \frac{hc}{4\pi\lambda_{ij}} \frac{Ng_i A_{ij}}{Z(T_{exc})} \exp\left(-\frac{E_i}{kT_{exc}}\right) \text{ with}$$

h Planck's constant,
c speed of light,
$\lambda_{ij}$ the wavelength of the transition under consideration from the higher state i to the lower state j,
$g_i$ the statistical weight of the initial energy level i of the emission line,
$A_{ij}$ the probability of transition for the line under consideration,
$Z(T_{exc})$ the partition function,
$E_i$ the energy of the excited level from which the transition takes place,
$T_{exc}$ the temperature of the plasma.

FIGS. 29 and 30 give an account of the presence of parasitic elements during the analysis of the biochips by the LIBS technique, these biochips being in particular silicon-based (the most widespread case of biochips with a glass substrate). If an inventory is made of the other parasitic elements that may be present:
  in the various compositions of the glass substrates: Al, C, Na, O, Ca, B, Ge, As, Fe, Ti, Ni, Zn, and/or
  in the backbone of the nucleic acids: C, N, O, and/or
  in the molecular self-assemblies for attaching the probes: Au, S, O, C, N, Br,
it so happens that only the three elements Si, Fe (Fe⁺) and C have lines that are more or less intense compared with those of phosphorus (see FIG. 29) in the spectral range [160 nm; 260 nm].

The graphs of FIGS. 29 and 30 record all the most intense lines of these various elements (and also those of phosphorus) in this spectral range and for a temperature of 13 000 K. It emerges therefrom that, by preferentially choosing to work at a wavelength above 200 nm, a set of phosphorus lines located at 203±3 nm appears to be particularly advantageous, by virtue of the compromise reaches between:
  the relative "distance" of this set of lines relative to the parasitic lines (presence of a less intense silicon line at 198.89 nm and of another, more intense, silicon line at 212.41 nm), it being specified that the use of an interference filter centered on 203 nm and having a spectral bandwidth of 3-6 nm is very suitable in this case; and
  the possibility of working, not on a single line, but on a set of lines of which the "cumulative" intensity is greater (by a factor of 4 to 5) than that of the phosphorus line at 253.56 nm.

As a variant, mention may be made of the use according to the invention of the phosphorus line at 213.61 nm, which is admittedly four times more intense than that at 253.56 nm, but which is only 12 Å from the silicon line at 212.41 nm mentioned above.

The graph of FIG. 30 shows in particular the study zone Z preferentially selected for the emission lines from phosphorus, on either side of 203 nm.

FIGS. 31 and 32 illustrate examples of plasma chambers 7 that can be used in a device for quantitative measurement according to the invention, in connection with means for controlling the atmosphere of the chamber and with the corresponding focusing optic.

With the LIBS technique, the obtaining of a plasma of optimal composition (i.e. allowing a fine spectral analysis) requires, as mentioned above, the use of a controlled atmosphere which is constituted of gases such as argon, neon or nitrogen. Each plasma confinement chamber 7, which may be machined in aluminum, for example (a material which is readily machinable and inexpensive), is positioned in these examples between the focusing optic (comprising lenses L, L') and the biochip 1 by being fixed to the microscope objective O, as illustrated in FIGS. 31 to 33. Each chamber 7 is thus fixed to the barrel of the focusing optic. An opening on the side of each chamber 7 which is connected to a tube 12 allows the input of the plasmagenic gas (see FIG. 8 commented on above) through this chamber 7.

For a diameter of this objective O equal to 25 mm and a working distance D of 10 mm, the geometry of each chamber 7 may, for example, result in a confinement of the atmosphere in a volume of less than 50 mm³. A space d left between the chamber 7 and the analytical surface of the biochip 1 (d<1 mm, preferably) allows the gas to be evacuated. The acquisition optic envisioned can be integrated into the structure of each chamber 7, as explained hereinafter.

The chamber 7 according to the invention of FIG. 32 is provided with an optical fiber 12' which passes through it laterally, in addition to the tube 12 supplying the plasmagenic gas.

In the embodiment according to the invention of FIGS. 33 and 34, the confinement chamber 7 has been replaced with a closed cell or chamber 7', for example of parallelepipedal shape, at least the upper face 7a' of which is made of quartz or of any other material that is transparent to the excitation and acquisition wavelengths. The chamber 7' is equipped on its lower face with two valves V1 and V2, respectively for filling with plasmagenic gas (e.g. argon/nitrogen) and for flushing of air. The air contained in the chamber 7' can thus be extracted by virtue of the flush valve V2, and then this chamber 7' is filled with plasmagenic gas by virtue of the filling valve V1. Also visible in these FIGS. 33 and 34 is a base S of a motorized platform on which the biochip 1 is mounted such that it can move in the directions X and Y of FIG. 6. The upper face 7a' of this cell allows the laser pulses to pass through so as to generate the plasma at the surface of the biochip 1 and the acquisition of the emission lines from the plasma by virtue of optical fibers 12' placed in proximity to this surface. It will be noted that the lateral faces of the cell 7' may optionally also be made of quartz, thus allowing excitation of the plasma by means of another laser beam placed on the side.

FIG. 35 illustrates, for a working distance D between the objective O of the microscope and the analytical surface of the biochip 1 which is chosen to be less than 10 mm, the homogeneous emission of the plasma P in a solid angle of $2\pi$ steradians, starting from the central point from where the radiation is emitted.

It will be noted that the minimum length of the or of each optical fiber would have to at least be equal to half the diameter of the objective O, in order to be able to place in position a detector. Be that as it may, an optical fiber length of greater than 10 cm is not necessary. At the output of the acquisition optical fibers 13', instead of using, in the case of the LIBS microprobe, a spectrometer inside which application of a more or less strong vacuum has been established, use may advantageously be made of another acquisition system of the type with an interference filter and with a "CPM" (channel photo multiplier) which is particularly suitable for a wavelength $\lambda$ close to 200 nm.

FIGS. 36 and 37 illustrate the principle optical characteristics of this acquisition unit 5' of the type with an optical fiber 13' and with an interference filter (reference 60 on the figures)/CPM (reference 70 on the figures). The optical fiber 13' may, for example, be a "Ocean Optics" fiber model with an NA (numerical aperture) of 0.22, i.e. 24.8°, and the CPM 70 joined to the interference filter may, for example, be a Perkin Elmer model.

The interference filter 60 (refractive index n1, thickness e1) advantageously relates to the wavelength for analysis of the phosphorus contained in the plasma P, for one of the characteristic wavelengths of phosphorus.

The CPM 70 is characterized by a quartz window 71 (with a refractive index n2 and a thickness e2) and by a multialkali photocathode (of thickness e3). As a variant, a photomultiplier of "PM" type, a microchannel wafer or even any other photon detector could be used in place of this CPM.

A layer 80 of air, of water of optical oil (air is preferentially used), designed so as to be transparent to the acquisition wavelength chosen, can also be seen in FIG. 37, for this acquisition unit 5', in addition to the interference filter 60 and to the CPM 70.

In another embodiment, it will be noted that a convergent lens could be introduced between the optical fiber 13' and the CPM 70, in order to image the fiber output on this CPM 70.

The invention claimed is:

1. A device for quantitative measurement of biomolecular targets, comprising:
   a biochip having a matrix of probes hybridized by biomolecular targets, said matrix comprising a multitude of measurement points each comprising a plurality of said probes,
   a plasma generating and confining unit configured for focusing at least one laser beam onto the measurement points in order to extract therefrom a hot plasma containing a chemical element to be quantified that is present in said targets and, optionally, also in said probes, the unit comprising means for confining the hot plasma thus extracted which comprise at least one arrangement of n (n>1) plasma chamber(s) delimited by an enclosure surmounting the biochip and being open over the biochip, and
   a spectrography unit which is connected to said plasma generating and confining unit and which is suitable for detecting and analyzing emission lines from the hot plasma for each measurement point, in such a way that the concentration in each measurement point of said chemical element is determined on the basis of a correlation between the intensities of the lines specific to said chemical element to be quantified and given concentrations of this element.

2. The device as claimed in claim 1, wherein said targets that hybridize said probes comprise unlabeled nucleic acids, and in that said probes are chosen from the group consisting of nucleic acids, peptide nucleic acids, locked nucleic acids and ribonucleic ethers.

3. The device as claimed in claim 2, wherein the size of each target is substantially equal to that of each probe, such that all the targets of each measurement point are hybridized.

4. The device as claimed in claim 1, wherein said enclosure is provided with excitation orifices which are each intended to receive an excitation laser beam capable of forming said hot plasma and having optical fibers for acquisition of the emission lines from the hot plasma passing through the enclosure for transmission of the emission lines to said spectrography unit, said at least one arrangement of n plasma chamber(s) moving relatively with respect to the biochip.

5. The device as claimed in claim 4, wherein said plasma generating and confining unit is configured for emitting a plurality of excitation laser beams and for conveying the plurality of excitation laser beams, respectively and simultaneously, inside said n plasma chamber(s) via said excitation orifices.

6. The device as claimed in claim 5, wherein said plurality of excitation laser beams are respectively derived from various laser sources.

7. The device as claimed in claim 5, wherein each of said excitation orifices of each of said n plasma chamber(s) receives an excitation optical fiber which is intended to guide each of said plurality of excitation laser beams corresponding to a given wavelength and which is provided, at a free end of the excitation optical fiber, with a first optical lens suitable for causing each of said plurality of excitation laser beams to converge onto the biochip.

8. The device as claimed in claim 5, wherein said plurality of excitation laser beams are derived from a single laser source which emits an upstream beam comprising several wavelengths which are 0.4 nm to 1 nm apart from one another, and a wavelength demultiplexer for separating this upstream beam into downstream beams having, respectively, as many wavelengths as there are excitation optical fibers intended to carry the downstream beams.

9. The device as claimed in claim 4, wherein said plasma generating unit is configured for emitting a single excitation laser beam and for conveying the single excitation laser beam successively inside said n plasma chambers by moving the single excitation laser beam from one excitation orifice to another via a galvanometer head.

10. The device as claimed in claim 5, wherein each of said n plasma chamber(s) is delimited by a lateral surface of revolution having a lower part, the top of said lateral surface of revolution being provided with one of said excitation orifices, which has on said lateral surface of revolution an acquisition orifice receiving one of said optical fibers for acquisition and which opens out immediately above the biochip via a lower opening of each of said n plasma chamber(s), so as to confine said hot plasma extracted therefrom by a corresponding laser beam of said plurality of excitation laser beams.

11. The device as claimed in claim 10, wherein each of said optical fibers for acquisition of each of said n plasma chambers is provided with a second optical lens at a free end of each of said optical fibers for acquisition emerging in each of said n plasma chamber(s), and in that an internal face of said lateral surface of revolution is designed so as to locally form a concave mirror capable of optimizing a reflection of light radiations emitted by said hot plasma in the direction of each of said optical fibers for acquisition.

12. The device as claimed in claim 10, wherein said n plasma chamber(s) consist(s) of several plasma chambers, said plasma generating unit being also configured for emitting a second-excitation laser beam and for introducing this beam from one of said several plasma chambers to another, via at least one second-excitation orifice made in said lower part of said lateral surface of revolution of each of said several plasma chambers at the height of expansion of the hot plasma or of expulsion of a material extracted from the biochip, each second-excitation orifice being made at a position planned so as not to be affected by each of said optical fibers for acquisition or by said concave mirror.

13. The device as claimed in claim 12, wherein said plasma generating unit comprises a galvanometer head capable of moving said second-excitation beam from one second-excitation orifice to another, for emitting said second-excitation beam and for introducing this beam from one of said several plasma chambers to another.

14. The device as claimed in claim 13, wherein each second-excitation orifice is provided with a third optical lens capable of causing said second-excitation laser beam to converge at said height of expansion of the hot plasma or of expulsion of a material extracted from the biochip.

15. The device as claimed in claim 12, wherein said several plasma chambers have several pairs of second-excitation orifices facing one another, such that said several pairs of second-excitation orifices form an alignment within said arrangement of said several plasma chambers for focusing, through the alignment said second-excitation laser beam.

16. The device as claimed in claim 1, wherein said measurement points respectively comprise magnetic or paramagnetic beads, each of the beads having a color different than that of the rest of the biochip and than that of the other measurement points, such that said magnetic or paramagnetic beads form optical test objects capable of being identified unequivocally by an image capture system with which said spectrography unit is equipped.

17. The device as claimed in claim 16, wherein the biochip comprises a plastic sheet forming a magnetic screen on which are made as many holes as there are said magnetic or paramagnetic beads, and which surmounts a magnetic strip capable of generating, in each of said holes, a magnetic field with an intensity of between 0.5 T and 5 T.

18. The device as claimed in claim 17, wherein each of said magnetic or paramagnetic beads is constituted of a lower half-sphere and an upper half-sphere which are bonded to one another in one of said holes and of which only the lower half-sphere turned toward said magnetic strip has paramagnetic properties, the upper half-sphere having a convex surface, said probes being grafted onto said convex surface which is colored so as to form one of said optical test objects.

19. The device as claimed in claim 17, wherein each of said magnetic or paramagnetic beads is constituted of a colored upper half-sphere having a convex surface, which is intended to form one of said optical test objects and onto said convex surface of which said probes are grafted, a cone having paramagnetic properties being bonded via its base under the edge of the upper half-sphere and on the side of said magnetic strip, inside said holes.

20. The device as claimed in claim 10, wherein said lateral surface of revolution of each of said n plasma chamber(s) is cylindrical or conical, becoming wider toward the biochip, between 2 mm and 10 mm in height and opens out at a distance from the biochip of between 5 μm and 200 μm, with a diameter for said lower opening which is between 1 mm and 5 mm.

21. The device as claimed in claim 10, wherein each of said n plasma chamber(s) is provided, in addition, with a gas injection orifice which is made on said lateral surface of revolution in immediate proximity to said excitation orifice and which receives a pipe intended to introduce an inert gas capable of depleting each of said n plasma chamber(s) of oxygen and of activating said hot plasma at the time said hot plasma is formed.

22. The device as claimed in claim 4, wherein said n plasma chamber(s) consists of several plasma chambers and the biochip, said n plasma chamber(s) is respectively mounted so that said several plasma chambers and the biochip can move along two orthogonal axes X and Y, in such a way that, with each movement of the biochip along the Y axis, said several plasma chambers make K movements along the X-axis, where:
  K is defined by the ratio P/l of the distance P between the respective excitation fibers of two adjacent chambers of said several chambers and of the width 1 along the X-axis of a surface ablated at each laser pulse, the ratio being modulated by the shape factor of an ablation after vaporization, and where
  the distance P between these two excitation fibers is defined by the equation $P = L/(N-1)$ with $N > 1$, L being the width of the biochip and N the number of excitation fibers in said several plasma chambers.

23. The device as claimed in claim 22, wherein the distance P between two adjacent excitation fibers is a multiple of a step between two measurement points on the biochip.

24. The device as claimed in claim 4, wherein said enclosure is provided with at least one solenoid suitable for generating therein a magnetic field to increase the lifetime of said hot plasma and/or to control the shape thereof.

25. The device as claimed in claim 4, wherein the device is provided with an electrically conducting material for a support of the biochip or else with an electrode carried by said support of the biochip with which is associated another electrode carried by said enclosure in order to generate a potential difference, so that in both cases an electric field is generated.

26. The device as claimed in claim 4, wherein said n plasma chamber(s) consist(s) of several plasma chambers, said enclosure having a substantially parallelepipedal geometry which is suitable for surrounding at least one line of said several plasma chambers, and which is formed by a laser or mechanical structuring technique using a powder or a liquid polymer.

27. The device as claimed in claim 1, wherein said spectrography unit comprises at least one spectrograph of photo-multiplied type, and in that an optical filter transparent only to the desired wavelength is placed between each of said acquisition optical fibers for acquisition and said spectrograph.

28. The device as claimed in claim 4, wherein said n plasma chamber(s) consist(s) of a single plasma chamber constituted of a closed enclosure containing said biochip, at least the upper face of which is made of quartz or of any other material transparent to the excitation and acquisition wavelengths, the closed enclosure being equipped with valves for filling with plasmagenic gas.

* * * * *